(12) United States Patent
Harada et al.

(10) Patent No.: US 6,320,102 B1
(45) Date of Patent: Nov. 20, 2001

(54) LEAFY COTYLEDON1 GENES AND THEIR USES

(75) Inventors: John J. Harada, Davis, CA (US); Tamar Lotan, Jordan Valley, IL (US); Masa-aki Ohto, Okazaki (JP); Robert B. Goldberg, Topanga; Robert L. Fischer, El Cerrito, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/193,931

(22) Filed: Nov. 17, 1998

Related U.S. Application Data

(63) Continuation-in-part of application No. 09/103,478, filed on Jun. 24, 1998, now Pat. No. 6,235,975, which is a continuation-in-part of application No. 09/026,221, filed on Feb. 19, 1998, which is a continuation-in-part of application No. 08/804,534, filed on Feb. 21, 1997, now abandoned.

(51) Int. Cl.⁷ .............................. A01H 4/00; A01H 5/00; C12N 15/29; C12N 15/74; C07H 21/02

(52) U.S. Cl. .................. 800/287; 800/278; 800/284; 800/290; 536/24.1; 536/23.1; 435/471

(58) Field of Search ................................. 800/278, 284, 800/287, 290; 536/24.1, 23.1; 435/471

(56) References Cited

PUBLICATIONS

Kim et al. Plant Molecular biology 1994. Vol. 24: 105–117.*
West, et al., "Leafy Coyledon1 Is An Essential Regulator of Late Embryogenesis and Cotyledon Identity in Arabidopsis"; *The Plant Cell*, vol. 6, 1731–1745 (Dec. 1994).
Meinke, et al., "Leafy Cotyledon Mutants of Arabidopsis", *The Plant Cell*, vol. 6, 1049–1064 (Aug. 1994).
Baumlein, et al., "The FUS3 Gene of *Arabidopsis thaliana* is a regulator of gene expression during late embryogenesis"; *The Plant Journal*, 6(3): 379–387 (1994).
Becker, et al., "A cDNA encoding a human CCAAT–binding protein cloned by functional complementation in yeast"; *Proc. Natl. Acad. Sci. USA*, vol. 88: 1968–1972 (Mar. 1991).
Sinha, et al., "Recombinant rat CBF–C, the third subunit of CBF/NFY, allows formation of a protein–DNA complex with CBF–A and CBF–B and with yeast HAP2 and HAP3"; *Proc. Natl. Acad. Sci. USA*, 1624–1628 (Feb. 1995).
Li, et al., "Evolutionary variation of the CCAAT–binding transcription factor NF–Y"; *Nucleic Acids Res.*, vol. 20, No. 5, 1087–1091 (Feb. 1992).

Johnson, et al., "Eukaryotic Transcriptional Regulatory Proteins"; *Annu. Rev. Biochem.*, 58:799–839 (1989).
Xing, et al. "Mutations in yeast HAP2/HAP3 define a hybrid CCAAT box binding domain"; *The EMBO J.*, vol. 12, No. 12, 4647–4655 (1993).
McCarty, et al., "The Viviparous–1 Developmental Gene of Maize Encodes a Novel Transcriptional Activator"; *Cell*, vol. 66, 895–905 (Sep. 1991).
McCarty, D. "Genetic Control and Integration of Maturation and Germination Pathways in Seed Development"; *Annu. Rev. Plant Physiol. Plant Mol. Biol.*, 46:71–93 (1995).
Giraudat, J., "Abscisic acid signaling"; *Current Opinion in Cell Biology*, 7:232–238 (1995).
Parcy, et al., "Regulation of Gene Expression Programs during Arabidopsis Seed Development: Roles of the AB13 Locus and of Endogenous Abscisic Acid"; *The Plant Cell*, vol. 6, 1567–1582 (Nov. 1994).
McCarty, et al., "Molecular Analysis of viviparous–1: An Abscisic Acid–Insensitive Mutant of Maize"; *The Plant Cell*, vol. 1, 523–532 (May 1989).
Heck, et al., "AGL15, a MADS Domain Protein Expressed in Developing Embryos"; *The Plant Cell*, vol. 7, 1271–1282 (Aug. 1995).
Valvekens, et al., "*Agrobacterium tumefaciens*–mediated transformation of *Arabidopsis thaliana* root explants by using kanamycin selection"; *Proc. Natl. Acad. Sci., USA*, vol. 85, 5536–5540 (Aug. 1988).
Ming–Tsair Chan, et al., "Novel Gene Expression System for Plant Cells Based on Induction of α–Amylase Promoter by Carbohydrate Starvation"; *The Journal of Biological Chemistry*, vol. 269, No. 26, 17635–17641 (Jul. 1994).
Shimada, et al., "Antisense regulation of the rice waxy gene expression using a PCR–amplified fragment of the rice genome reduces the amylose content in grain starch"; *Theoretical and Applied Genetics*, vol. 86, 665–672 (Jan. 1993).
Meinke, David, "A Homoeotic Mutant of *Arabidopsis thaliana* with Leafy Cotyledons"; *Science*, vol. 258, 1647–1650, (Dec. 1992).

\* cited by examiner

Primary Examiner—Paula K. Hutzell
Assistant Examiner—O. M. F. Zaghnout
(74) Attorney, Agent, or Firm—Townsend and Townsend and Crew LLP

(57) ABSTRACT

The present invention provides nucleic acid sequences from embryo-specific genes. The nucleic acids are useful in targeting gene expression to zygotes and embryos or in modulating embryo development.

9 Claims, 2 Drawing Sheets

SEQUENCE LISTING

```
<160> NUMBER OF SEQ ID NOS: 29

<210> SEQ ID NO 1
<211> LENGTH: 627
<212> TYPE: DNA
<213> ORGANISM: Arabidopsis thaliana
<220> FEATURE:
<221> NAME/KEY: CDS
<222> LOCATION: (1)..(627)
<223> OTHER INFORMATION: LEAFY COTYLEDON1 (LEC1)

<400> SEQUENCE: 1 atg acc agc tca gtc ata gta gcc ggc gcc ggt gac aag aac aat ggt      48
Met Thr Ser Ser Val Ile Val Ala Gly Ala Gly Asp Lys Asn Asn Gly
 1               5                  10                  15 atc gtg gtc cag cag caa cca cca tgt gtg gct cgt gag caa gac caa      96
Ile Val Val Gln Gln Gln Pro Pro Cys Val Ala Arg Glu Gln Asp Gln
             20                  25                  30 tac atg cca atc gca aac gtc ata aga atc atg cgt aaa acc tta ccg     144
Tyr Met Pro Ile Ala Asn Val Ile Arg Ile Met Arg Lys Thr Leu Pro
         35                  40                  45 tct cac gcc aaa atc tct gac gac gcc aaa gaa acg att caa gaa tgt     192
Ser His Ala Lys Ile Ser Asp Asp Ala Lys Glu Thr Ile Gln Glu Cys
     50                  55                  60 gtc tcc gag tac atc agc ttc gtg acc ggt gaa gcc aac gag cgt tgc     240
Val Ser Glu Tyr Ile Ser Phe Val Thr Gly Glu Ala Asn Glu Arg Cys
 65                  70                  75                  80 caa cgt gag caa cgt aag acc ata act gct gaa gat atc ctt tgg gct     288
Gln Arg Glu Gln Arg Lys Thr Ile Thr Ala Glu Asp Ile Leu Trp Ala
                 85                  90                  95 atg agc aag ctt ggg ttc gat aac tac gtg gac ccc ctc acc gtg ttc     336
Met Ser Lys Leu Gly Phe Asp Asn Tyr Val Asp Pro Leu Thr Val Phe
            100                 105                 110 att aac cgg tac cgt gag ata gag acc gat cgt ggt tct gca ctt aga     384
Ile Asn Arg Tyr Arg Glu Ile Glu Thr Asp Arg Gly Ser Ala Leu Arg
        115                 120                 125 ggt gag cca ccg tcg ttg aga caa acc tat gga gga aat ggt att ggg     432
Gly Glu Pro Pro Ser Leu Arg Gln Thr Tyr Gly Gly Asn Gly Ile Gly
    130                 135                 140
```

```
ttt cac ggc cca tct cat ggc cta cct cct ccg ggt cct tat ggt tat      480
Phe His Gly Pro Ser His Gly Leu Pro Pro Pro Gly Pro Tyr Gly Tyr
145                 150                 155                 160 ggt atg ttg gac caa tcc atg gtt atg gga ggt ggt cgg tac tac caa      528
Gly Met Leu Asp Gln Ser Met Val Met Gly Gly Gly Arg Tyr Tyr Gln
                165                 170                 175 aac ggg tcg tcg ggt caa gat gaa tcc agt gtt ggt ggt gct tct          576
Asn Gly Ser Ser Gly Gln Asp Glu Ser Ser Val Gly Gly Ser Ser
            180                 185                 190 tct tcc att aac gga atg ccg gct ttt gac cat tat ggt cag tat aag      624
Ser Ser Ile Asn Gly Met Pro Ala Phe Asp His Tyr Gly Gln Tyr Lys
        195                 200                 205 tga                                                                    627

<210> SEQ ID NO 2
<211> LENGTH: 208
<212> TYPE: PRT
<213> ORGANISM: Arabidopsis thaliana

<400> SEQUENCE: 2

Met Thr Ser Ser Val Ile Val Ala Gly Ala Gly Asp Lys Asn Asn Gly
 1               5                  10                  15

Ile Val Val Gln Gln Gln Pro Pro Cys Val Ala Arg Glu Gln Asp Gln
             20                  25                  30

Tyr Met Pro Ile Ala Asn Val Ile Arg Ile Met Arg Lys Thr Leu Pro
         35                  40                  45

Ser His Ala Lys Ile Ser Asp Asp Ala Lys Glu Thr Ile Gln Glu Cys
     50                  55                  60

Val Ser Glu Tyr Ile Ser Phe Val Thr Gly Glu Ala Asn Glu Arg Cys
 65                  70                  75                  80

Gln Arg Glu Gln Arg Lys Thr Ile Thr Ala Glu Asp Ile Leu Trp Ala
                 85                  90                  95

Met Ser Lys Leu Gly Phe Asp Asn Tyr Val Asp Pro Leu Thr Val Phe
            100                 105                 110

Ile Asn Arg Tyr Arg Glu Ile Glu Thr Asp Arg Gly Ser Ala Leu Arg
        115                 120                 125

Gly Glu Pro Pro Ser Leu Arg Gln Thr Tyr Gly Gly Asn Gly Ile Gly
    130                 135                 140

Phe His Gly Pro Ser His Gly Leu Pro Pro Pro Gly Pro Tyr Gly Tyr
145                 150                 155                 160

Gly Met Leu Asp Gln Ser Met Val Met Gly Gly Gly Arg Tyr Tyr Gln
                165                 170                 175

Asn Gly Ser Ser Gly Gln Asp Glu Ser Ser Val Gly Gly Ser Ser
            180                 185                 190

Ser Ser Ile Asn Gly Met Pro Ala Phe Asp His Tyr Gly Gln Tyr Lys
        195                 200                 205

<210> SEQ ID NO 3
<211> LENGTH: 3395
<212> TYPE: DNA
<213> ORGANISM: Arabidopsis thaliana
<220> FEATURE:
<223> OTHER INFORMATION: 3.4 kb BstyI fragment of genomic DNA containing
      LEC1 gene
<221> NAME/KEY: promoter
<222> LOCATION: (1)..(1998)
<223> OTHER INFORMATION: LEC1 promoter
<221> NAME/KEY: CDS
<222> LOCATION: (1999)..(2625)
```

<223> OTHER INFORMATION: LEAFY COTYLEDON1 (LEC1)
<221> NAME/KEY: modified_base
<222> LOCATION: (1) .. (3395)
<223> OTHER INFORMATION: n = g , a, c, or t

<400> SEQUENCE: 3

| | | | | | |
|---|---|---|---|---|---|
| agatccaaaa | caggtcatgg | actgggccgt | aaactctatc | caaaattctt | catgtttttc | 60 |
| catctttcaa | aaatctttat | ccaccattcc | attactaggg | tgttggtttt | attttatttg | 120 |
| ttgattaatt | atgtattaga | aaatgtaaag | caatattcaa | ttgtaacatg | catcatctaa | 180 |
| caccaatatc | ttgtactaac | cttttgtaat | tttcctataa | acattttaaa | aggctaattt | 240 |
| aaataaaaat | tacaataaac | gtgataactc | actttcgtaa | cgcatattta | ttcaaatata | 300 |
| ccaaaattta | ccattttaag | taagagaatc | tttttaaaat | taattttcaa | tttcattaat | 360 |
| taagaaacaa | agaatttact | gaaacctata | ttttattaaa | ttttaataaa | atatatgact | 420 |
| aaaataacgt | cacgtgaatc | tttctcagcc | gttcgataat | cgaatacttt | attgactaag | 480 |
| tatttattta | gaaaatttta | aacaacactt | aatttctaga | acaaagaga | gcctcatatg | 540 |
| tataaaaatc | ttcttcttat | ctttctttct | ttcttaatag | tctttatttt | tacttaatta | 600 |
| ctttggtaat | ttgtgaaaaa | cacaaccaat | gagagaagag | cagtttgact | ggccacatag | 660 |
| ccaatgagac | aagccaatgg | gaaagagata | tagagacctc | gtaagaaccg | ctcctttgcc | 720 |
| atttgtatca | tctctctata | aaaccactca | accatcaacc | tntctttgca | tgcaacaaat | 780 |
| cactcaaata | attattttat | aaagaacaaa | aaaaaaaaga | cggcagagaa | acaatggaac | 840 |
| gtggagctcc | cttctctcac | tatcagctac | ccaaatccat | ctctggtaat | ctaagtggct | 900 |
| atttgtatac | agtatatact | tgcctccatg | tatatttata | ttctcgtgaa | aaattggaga | 960 |
| catgctttat | gaatttatg | agactttgca | acaacgaacg | agatgctttc | tctctagaaa | 1020 |
| tttaaattta | gatttgtgaa | ggttttggga | atggcccgga | gaagacgatt | ttatatatac | 1080 |
| atgcatgcaa | gagtttgata | tgtatattgt | ttcatcatgg | ctgagtcaaa | gttttatcca | 1140 |
| aatatttcca | tggtgtggta | ttagttaaac | aaatctctcg | tatgtgtcat | tgaatatacc | 1200 |
| cgtgcatgta | ccaggaatgt | ttttgattct | aaaaacgttt | ttttctttgt | tgtaacggtt | 1260 |
| gagttttttt | cttcgtttca | aaacgagatt | ctcgtttgtc | tcttcccttg | tctaaaaaca | 1320 |
| tctacggttc | atgtgattca | aaaacactaa | aaaaatataa | actcattttt | ttttaatact | 1380 |
| taacatttaa | actatatata | tatatatata | tatatatatc | ttatactagt | cccaagtttt | 1440 |
| agtgtgaggt | tttttattc | aaaatctatc | agtacatttt | ttggaaaaga | actaagtgaa | 1500 |
| attttctcca | aattttcctt | ttactattga | ttttttaatt | actggatgtc | attaacttta | 1560 |
| atcttttgat | tctttcaacg | tttaccattg | ggaaccttca | catgaaataa | atgtctactt | 1620 |
| tattgagtca | taccttcgtc | aacataaatt | aattgatgtt | cttctccaaa | ttttgagttt | 1680 |
| ttggtttttc | taataatctt | aacgaaagct | ttttggtata | catgtaaaac | gtaacggcaa | 1740 |
| gaatctgaac | agtctactca | acggggtcca | taagtctaga | atgtagaccc | cacaaactta | 1800 |
| ctcttatctt | attggtccgt | aactaagaac | gtgtccctct | gattctcttg | ttttcttcta | 1860 |
| attaattcgt | atcctacaaa | tttaattatc | atttctactt | caactaatct | ttttttattt | 1920 |
| cctaaagatt | tcaatttctc | tctgtattt | ctatgaacag | aattgaactt | ggaccagcac | 1980 |
| agcaacaacc | caacccaat | gaccagctca | gtcatagtag | ccggcgccgg | tgacaagaac | 2040 |
| aatggtatcg | tggtccagca | gcaaccacca | tgtgtggctc | gtgagcaaga | ccaatacatg | 2100 |
| ccaatcgcaa | acgtcataag | aatcatgcgt | aaaacccttac | cgtctcacgc | caaaatctct | 2160 |

```
gacgacgcca aagaaacgat tcaagaatgt gtctccgagt acatcagctt cgtgaccggt    2220
gaagccaacg agcgttgcca acgtgagcaa cgtaagacca taactgctga agatatcctt    2280
tgggctatga gcaagcttgg gttcgataac tacgtggacc ccctcaccgt gttcattaac    2340
cggtaccgtg agatagagac cgatcgtggt tctgcactta gaggtgagcc accgtcgttg    2400
agacaaacct atggaggaaa tggtattggg tttcacggcc catctcatgg cctacctcct    2460
ccgggtcctt atggttatgg tatgttggac caatccatgg ttatgggagg tggtcggtac    2520
taccaaaacg ggtcgtcggg tcaagatgaa tccagtgttg gtggtggctc ttcgtcttcc    2580
attaacggaa tgccggcttt tgaccattat ggtcagtata agtgaagaag gagttattct    2640
tcatttttat atctattcaa acatgtgtt cgatagata ttttattttt atgtcttatc    2700
aataacattt ctatataatg ttgcttcttt aaggaaaagt gttgtatgtc aatactttat    2760
gagaaactga tttatatatg caatgattga atccaaact gttttgtgga ttaaactcta    2820
tgcaacatta tatatttaca tgatctaaag gttttgtaat tcaaaagctg tcatagttag    2880
aagataacta acattgtag taaccaagtt taatttactt ttttgagttt acataactaa    2940
ccaagccaaa aggttataaa atctaaattc gttgagttgt caaacttctg aagattgcta    3000
tcctctttga gttgctttct tttgggtgct tgagtttcat taggctgagc tgactcgttg    3060
ctctctagtc tttcatctct gtcttttcca aggattcata acgttggtcg ctctctgttt    3120
ctgcctacac ttcttcaagg gatcattact gaggctaaga gttaaagacc tgaaccatgg    3180
ttttctgtaa ctggttcaag ttcattctcc ggttattgtg tggttatctt tcggttagat    3240
tgaaacccat atgtttgctc tgtttcttct agttccaagt ttaatttccg gttattgttt    3300 ggcttttaa aagttttaa ggtctattct atgtaaagac tattctacgt acgtacattt    3360
atcgcaaaat tgaaagatta taaaaaaaat tgaaa                              3395
```

<210> SEQ ID NO 4
<211> LENGTH: 7560
<212> TYPE: DNA
<213> ORGANISM: Arabidopsis thaliana
<220> FEATURE:
<223> OTHER INFORMATION: 7.4 kb genomic wild-type fragment containing
      LEC1 gene
<221> NAME/KEY: misc_feature
<222> LOCATION: (2430)..(5824)
<223> OTHER INFORMATION: corresponds to SEQ ID NO:3
<221> NAME/KEY: promoter
<222> LOCATION: (2430)..(4427)
<223> OTHER INFORMATION: corresponds to LEC1 promoter in SEQ ID NO:3
<221> NAME/KEY: CDS
<222> LOCATION: (4427)..(5054)
<223> OTHER INFORMATION: LEAFY COTYLEDON1 (LEC1)
<221> NAME/KEY: modified_base
<222> LOCATION: (1) .. (7560)
<223> OTHER INFORMATION: n = g, a, c or t

<400> SEQUENCE: 4

```
aattnaccct cactaaaggg aacaaaagct gggtaccggg ccccccctcg aggtcgacgg      60
tatcgataag cttgatatcg aattcgtggc cattagaccc ataactatat gacgatgtta    120
aagagaaaat aaatcataaa taaaataaga gtccttatca ataaacctaa ttggctaatt    180
tcaacctcaa agagtagtag gaacaggtaa ggtgaagcca aacagctcct tttacagttg    240
gaccactaga gctgatctgg catacaaagt atgcttattg ggctgtcacg gcccatccgc    300
aaaatgtcgt tggttacgaa gcatccacga catagacggt gccacatgtt agaaaagtgt    360
ttcggcgatc aagattgtgt ccacatcatt agacgtctga actgtccacg tgtctatcaa    420
```

-continued

```
agctggcgtc aaacattacg ttttcgtcgt ttgcgcctcc tagttcacac gtgcaacgaa    480
cgcgtgcgac gtatcaaaat tgttaatttt agccatgtat aaagaatatc tacaaaatta    540
acctcaggaa tattttttgtt ttttcaattg aggccataat atacntnccg atngaaaaat    600
tttncancat atcnctaata tcaaaaaatt atgatgttag taaacgtaaa aaatttacac    660
aaaataantt tcacaaaact tannggggaa attggaacaa anaaaagact ggtgagtgat    720
aagcgatgat ggccggtgaa tcaggtagcc gtcctacaac gtggttgatt ttgagcaaac    780
tcctatctac tcttcacact attggaaatc ccaaaatgtc gtcacaccat aataatgtga    840
attttgttat ggaatttgag ggaaacagta gatatatgtt tcaaccagtg aaagttaccc    900
tcctttggac atatctacga nagtagaaag tagaaacatt cactaaacgt gacaacttta    960
taaattttct ttttgtaact tttctttaga tttatttacg anaagagaaa tataaacgtc   1020
atgctaataa aaaatgcatt attttctacc atctagctag aatattgatc aagtcttcac   1080
gttttttgtt tatctcttct ctcataggca tgtccacaaa agggtaagtt ttactggttc   1140
aaaatattgc atgagtacta ctaagctcgt atagtttgat cttactatca ttgcgatgag   1200
ggttgttagt ttggaagaaa taaggattta tgcaaatggt aatcattatg tctgctattt   1260
aagaagtaaa ttatgatgct tgttgcgtga acatattaaa tttgcgaaaa ataagcaagg   1320
atacacgaga gaagctcaga tattcacgta acgatgtttc atctcttctc attgaggaaa   1380
catatggcca tgatatagct aataagccta cgggattgtc ntttcaacgc cgaatctacc   1440
aaactgttcc atctcttatt atatatagtt tggttattta agtaattaga tgcatcataa   1500 tcttttttc tgccagttgt aatgcagata aaaatatatt ggttgttcta aggattgttc   1560
aaacgtgcat gtgtacaagt tattatttat atactttcat ctacatgcga tgcgttattt   1620
ataatgataa aactaagatt tttagttaaa tttaataaag agcttacgag ctacaattaa   1680
ttagaaatgg ttgctcagaa atcagaatac tatatatgaa aaaagaagtt ggtatacttg   1740
aaaaaagaaa aaactacttg aaaagatggt aaaagatata gaacgagtat atatcttact   1800
caagcacgat agaagtttgt atcaaaacat tgcgttccaa accaatgttt gaagatggtc   1860
aaaggtgcta ctcatgatgt ggtgcgaaga agcttacgaa aaattctgca atgagagata   1920
actttatggg ctgcttgttc aatatattga aaatcatggt agacaacacc aaactctcct   1980
ttaccagaag tcatatttcc ttaacctcag aataagtaaa tcttctagtt tattatttga   2040
aagttgagcg tataattgca atgaaacttt taccaattca ccgcctccta actgagttgt   2100
tgtattatcc tatctcttta gctatccttt ccttgctctt gctccacctg catgtggcct   2160
ctttatttat aatctctcta gattctgcta agatgtntg ttcaaaatgg tttatcttta   2220
agggaagcaa agtgaatgga aacatttaaa gaaaaaaaa acttttagca gagttccatg   2280
agatttcata ctgatgataa ctaaaataat cttatatgcg taagattatt ttagttctaa   2340
acttcatttt gaaatgagag gtcattggcc aggaaagatt caatattggt tctttgttaa   2400
ttctcgttgg tttgttttta gtatgggcta gatccaaaac aggtcatgga ctgggccgta   2460
aactctatcc aaaattcttc atgttttttcc atctttcaaa aatctttatc caccattcca   2520
ttactagggt gttggtttta ttttatttgt tgattaatta tgtattagaa aatgtaaagc   2580
aatattcaat tgtaacatgc atcatctaac accaatatct tgtactaacc ttttgtaatt   2640
ttcctataaa catttaaaaa ggctaattta aataaaaatt acaataaacg tgataactca   2700
ctttcgtaac gcatatttat tcaaatatac caaaatttac catttttaagt aagagaatct   2760 ttttaaaatt aattttcaat ttcattaatt aagaaacaaa gaatttactg aaacctatat   2820
```

```
tttattaaat tttaataaaa tatatgacta aataacgtc acgtgaatct ttctcagccg      2880
ttcgataatc gaatacttta ttgactaagt atttatttag aaaattttaa acaacactta     2940
atttctagaa acaaagagag cctcatatgt ataaaaatct tcttcttatc tttctttctt     3000
tcttaatagt ctttattttt acttaattac tttggtaatt tgtgaaaaac acaaccaatg     3060
agagaagagc agtttgactg gccacatagc caatgagaca agccaatggg aaagagatat     3120
agagacctcg taagaaccgc tcctttgcca tttgtatcat ctctctataa aaccactcaa     3180
ccatcaacct ntctttgcat gcaacaaatc actcaaataa ttattttata aagaacaaaa     3240
aaaaaaagac ggcagagaaa caatggaacg tggagctccc ttctctcact atcagctacc     3300
caaatccatc tctggtaatc taagtggcta tttgtataca gtatatactt gcctccatgt     3360
atatttatat tctcgtgaaa aattggagac atgctttatg aattttatga gactttgcaa     3420
caacgaacga gatgctttct ctctagaaat ttaaatttag atttgtgaag gttttgggaa     3480
tggcccggag aagacgattt tatatataca tgcatgcaag agtttgatat gtatattgtt     3540
tcatcatggc tgagtcaaag ttttatccaa atatttccat ggtgtggtat tagttaaaca     3600
aatctctcgt atgtgtcatt gaatataccc gtgcatgtac caggaatgtt tttgattcta     3660
aaaacgtttt tttctttgtt gtaacggttg agttttttc ttcgtttcaa aacgagattc      3720
tcgtttgtct cttcccttgt ctaaaaacat ctacggttca tgtgattcaa aaacactaaa     3780
aaaatataaa ctcatttttt tttaatactt aacatttaaa ctatatatat atatatatat     3840
atatatatct tatactagtc ccaagtttta gtgtgaggtt ttttattca aaatctatca      3900 gtacattttt tggaaaagaa ctaagtgaaa ttttctccaa atttttccttt tactattgat    3960 tttttaatta ctggatgtca ttaactttaa tcttttgatt ctttcaacgt ttaccattgg     4020
gaaccttcac atgaaataaa tgtctacttt attgagtcat accttcgtca acataaaatta    4080 attgatgttc ttctccaaat tttgagtttt tggttttct aataatctta acgaaagctt      4140
tttggtatac atgtaaaacg taacggcaag aatctgaaca gtctactcaa cggggtccat     4200
aagtctagaa tgtagacccc acaaacttac tcttatctta ttggtccgta actaagaacg     4260
tgtccctctg attctcttgt tttcttctaa ttaattcgta tcctacaaat ttaattatca     4320
tttctacttc aactaatctt tttttatttc ctaaagattt caatttctct ctgtattttc     4380
tatgaacaga attgaacttg gaccagcaca gcaacaaccc aaccccaatg accagctcag     4440
tcatagtagc cggcgccggt gacaagaaca atggtatcgt ggtccagcag caaccaccat     4500
gtgtggctcg tgagcaagac caatacatgc caatcgcaaa cgtcataaga atcatgcgta     4560
aaaccttacc gtctcacgcc aaaatctctg acgacgccaa agaaacgatt caagaatgtg     4620
tctccgagta catcagcttc gtgaccggtg aagccaacga gcgttgccaa cgtgagcaac     4680
gtaagaccat aactgctgaa gatatccttt gggctatgag caagcttggg ttcgataact     4740
acgtggaccc cctcaccgtg ttcattaacc ggtaccgtga gatagagacc gatcgtggtt     4800
ctgcacttag aggtgagcca ccgtcgttga gacaaaccta tggaggaaat ggtattgggt     4860
ttcacggccc atctcatggc ctacctcctc cgggtcctta tggttatggt atgttggacc     4920
aatccatggt tatgggaggt ggtcggtact accaaaacgg gtcgtcgggt caagatgaat     4980
ccagtgttgg tggtggctct tcgtcttcca ttaacggaat gccggctttt gaccattatg     5040
gtcagtataa gtgaagaagg agttattctt cattttata tctattcaaa acatgtgttt      5100
cgatagatat tttatttta tgtcttatca ataacatttc tatataatgt tgcttcttta      5160
```

```
aggaaaagtg ttgtatgtca atactttatg agaaactgat ttatatatgc aaatgattga    5220
atccaaactg ttttgtggat taaactctat gcaacattat atatttacat gatctaaagg    5280
ttttgtaatt caaaagctgt catagttaga agataactaa acattgtagt aaccaagttt    5340
aatttacttt tttgagttta cataactaac caagccaaaa ggttataaaa tctaaattcg    5400
ttgagttgtc aaacttctga agattgctat cctctttgag ttgctttctt ttgggtgctt    5460
gagtttcatt aggctgagct gactcgttgc tctctagtct ttcatctctg tcttttccaa    5520
ggattcataa cgttggtcgc tctctgtttc tgcctacact tcttcaaggg atcattactg    5580
aggctaagag ttaaagacct gaaccatggt tttctgtaac tggttcaagt tcattctccg    5640
gttattgtgt ggttatcttt cggttagatt gaaacccata tgtttgctct gtttcttcta    5700
gttccaagtt taatttccgg ttattgtttg ctttttaaa agttttaag gtctattcta    5760 tgtaaagact attctacgta cgtacattta tcgcaaaatt gaaagattat aaaaaaaatt    5820
gaaagatcca aggaaacca atagattaaa ctaaaatgta gtatccttt tatcatttta    5880 ggctatgttt tcttttaaga aagctttggt agttaactct gtttaaaaga aaaaaaagag    5940
atgcataaat taaatttaag tttctagaac ttttggataa acatattaag ctaaagaaat    6000
taaactaaag ggcgtaaatg caagcttgtt atgcgttatt gaaacatta cctctaaatt    6060 aaatagccca atattgaaaa ccttaagctt ctttgatccc cttaacttgt ttgtccacca    6120
agtattagtt catctcttaa cacggcaact cgaaacggca caatggacaa acatggtctt    6180
tcaaaaacca cttcccaata catccatcgt caaactcgtg ccacatggt aaggtcacca    6240 ctatttctcc ctttttcaaac tcctccaaac aaattgtgca cacactggcg tcagagttgg    6300
atttcttctt attattatat actttccttg ccaaacggtc aaccacaaac ttatttgccg    6360
gtctaattaa ctcgatatta ttggtggtct catcaaacga gtcaatccga ggaggaggtg    6420
gaacaatgac tttacagtac atgtaaacta acgtagcaca aactgaagag tctaccatag    6480
aaatcgactt acagattcgt tcagtgagtt gagagttagc aatgtcaaca tattgttcgg    6540
agagccctgc tgagtacaac cattcattca gttttttcga gtcattaggg taggaggata    6600
tgacaccttc gtagtcattg tacgagagaa cgaaatttgg tggaagacta attgatgtgt    6660
ccgatcttcg ggcacttacg cagattttga atgatccagc atcttgtgat ttcggtttga    6720
ggtctatttc gccgccaaag gatatttccg cttccatagc tatcaaagag aaagaaaaat    6780
agtgaatcca aggtttaggg tttcttttct ttgtcttnct tatatataga ggcgctagat    6840
tgtattaagg attatacata tatataagta attgcaattt gtgagtttat ccttattcat    6900
ttttaatttt atttaccttt atttagttga tattgtgtcc ttttcctagg tagcatttcc    6960
ttccatctgt gttaattatt agcatttcct ttcctttgtc ttatttgcct ttatttcgta    7020
ggaagaaatc ctttatgnac cccatcttgg ctgagaactt gagatgattt taaatcctca    7080
aaaattattc aatttatgat ttcgaaattg atatacactt tatattttct cctaaaaaac    7140
catattgtac taagaaaagt agaaaaccag acttttaat atgttagatt ttaattgggt    7200
tcttaaagtg ttttagcgtt tnacaccggt tattctccaa aatccaaact ctataattat    7260 agttttaag tataaattaa tccggttggc ccaattagtg gaccgtttaa agagtagaca    7320
cttttttttt tatatatcga ctaccataaa actttaacga ttaatatttt tggataataa    7380
gcgatcgttt tgaggcgtcc caattttttt tgtttctttt tatatgagaa atgggtttaa    7440
gaaaaactgc aattttgtcc ataaagctag tcagaattcc tgcagcccgg gggatccact    7500
agttctagag cggccgccac cgcggtggag ctccaattcg ccctatagtg agtcgtatta    7560
```

```
<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence:DNA binding
      region of HAP3 subunit of CCAAT box-binding factor(CBF) protein B
      domain homolog with transcription activation function

<400> SEQUENCE: 5

Met Pro Ile Ala Asn Val Ile
  1               5

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence:subunit
      interaction domain of HAP3 subunit of CCAAT box-binding factor
      (CBF) protein B domain homolog

<400> SEQUENCE: 6

Ile Gln Glu Cys Val Ser Glu Tyr Ile Ser Phe Val
  1               5                  10

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:UP primer

<400> SEQUENCE: 7
ggaattcagc aacaacccaa cccca                                           25

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:LP primer

<400> SEQUENCE: 8
gctctagaca tacaacactt ttcctta                                         27

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:alternative
      primer

<400> SEQUENCE: 9
atgaccagct cagtcatagt agc                                             23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:alternative
      primer

<400> SEQUENCE: 10
```

```
gccacacatg gtggttgctg ctg                                              23
```

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:alternative
      primer

<400> SEQUENCE: 11

```
gagatagaga ccgatcgtgg ttc                                              23
```

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:alternative
      primer

<400> SEQUENCE: 12

```
tcacttatac tgaccataat ggtc                                             24
```

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:left border
      specific primer

<400> SEQUENCE: 13

```
gcatagatgc actcgaaatc agcc                                             24
```

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:T-DNA left
      border specific primer

<400> SEQUENCE: 14

```
gcttggtaat aattgtcatt ag                                               22
```

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:H21 primer

<400> SEQUENCE: 15

```
ctaaaaacat ctacggttca                                                  20
```

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:H17 primer

<400> SEQUENCE: 16

```
tttgtggttg accgtttggc                                                  20
```

```
<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:DNA binding
      region of HAP3 subunit of CCAAT box-binding factor (CBF-A) protein
      yeast homolog

<400> SEQUENCE: 17

Leu Pro Ile Ala Asn Val Ala
 1               5

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence:subunit
      interaction domain of HAP3 subunit of CCAAT box-binding factor
      (CBF-A) protein yeast homolog

<400> SEQUENCE: 18

Met Gln Glu Cys Val Ser Glu Phe Ile Ser Phe Val
 1               5                  10

<210> SEQ ID NO 19
<211> LENGTH: 90
<212> TYPE: PRT
<213> ORGANISM: Arabidopsis thaliana
<220> FEATURE:
<221> NAME/KEY: DOMAIN
<222> LOCATION: (1)..(90)
<223> OTHER INFORMATION: LEC1 HAP3 subunit of CCAAT box-binding factor
      (CBF) protein B domain homolog

<400> SEQUENCE: 19

Arg Glu Gln Asp Gln Tyr Met Pro Ile Ala Asn Val Ile Arg Ile Met
 1               5                  10                  15

Arg Lys Thr Leu Pro Ser His Ala Lys Ile Ser Asp Asp Ala Lys Glu
                20                  25                  30

Thr Ile Gln Glu Cys Val Ser Glu Tyr Ile Ser Phe Val Thr Gly Glu
            35                  40                  45

Ala Asn Glu Arg Cys Gln Arg Glu Gln Arg Lys Thr Ile Thr Ala Glu
        50                  55                  60

Asp Ile Leu Trp Ala Met Ser Lys Leu Gly Phe Gln Asn Tyr Val Asp
 65                 70                  75                  80

Pro Leu Thr Val Phe Ile Asn Arg Tyr Arg
                85                  90

<210> SEQ ID NO 20
<211> LENGTH: 90
<212> TYPE: PRT
<213> ORGANISM: Zea mays
<220> FEATURE:
<221> NAME/KEY: DOMAIN
<222> LOCATION: (1)..(90)
<223> OTHER INFORMATION: maize HAP3 subunit of CCAAT box-binding factor
      (CBF) protein B domain homolog

<400> SEQUENCE: 20

Arg Glu Gln Asp Arg Phe Leu Pro Ile Ala Asn Ile Ser Arg Ile Met
 1               5                  10                  15

Lys Lys Ala Ile Pro Ala Asn Gly Lys Ile Ala Lys Asp Ala Lys Glu
                20                  25                  30
```

```
Thr Val Gln Glu Cys Val Ser Glu Phe Ile Ser Phe Ile Thr Ser Glu
            35                  40                  45

Ala Ser Asp Lys Cys Gln Arg Glu Lys Arg Lys Thr Ile Asn Gly Asp
 50                  55                  60

Asp Leu Leu Trp Ala Met Ala Thr Leu Gly Phe Glu Asp Tyr Ile Glu
 65                  70                  75                  80

Pro Leu Lys Val Tyr Leu Gln Lys Tyr Arg
                 85                  90

<210> SEQ ID NO 21
<211> LENGTH: 90
<212> TYPE: PRT
<213> ORGANISM: Gallus sp.
<220> FEATURE:
<221> NAME/KEY: DOMAIN
<222> LOCATION: (1)..(90)
<223> OTHER INFORMATION: chicken HAP3 subunit of CCAAT box-binding
      factor (CBF) protein B domain homolog

<400> SEQUENCE: 21

Arg Glu Gln Asp Ile Tyr Leu Pro Ile Ala Asn Val Ala Arg Ile Met
 1               5                  10                  15

Lys Asn Ala Ile Pro Gln Thr Gly Lys Ile Ala Lys Asp Ala Lys Glu
                 20                  25                  30

Cys Val Gln Glu Cys Val Ser Glu Phe Ile Ser Phe Ile Thr Ser Glu
            35                  40                  45

Ala Ser Glu Arg Cys His Gln Lys Leu Arg Lys Thr Ile Asn Gly Glu
 50                  55                  60

Asp Ile Leu Phe Ala Met Ser Thr Leu Gly Phe Gln Ser Tyr Val Glu
 65                  70                  75                  80

Pro Leu Lys Leu Tyr Leu Gln Lys Phe Arg
                 85                  90

<210> SEQ ID NO 22
<211> LENGTH: 90
<212> TYPE: PRT
<213> ORGANISM: Petromyzontidae gen. sp.
<220> FEATURE:
<221> NAME/KEY: DOMAIN
<222> LOCATION: (1)..(90)
<223> OTHER INFORMATION: lamprey HAP3 subunit of CCAAT box-binding
      factor (CBF) protein B domain homolog

<400> SEQUENCE: 22

Arg Glu Gln Asp Ile Tyr Leu Pro Ile Ala Asn Val Ala Arg Ile Met
 1               5                  10                  15

Lys Thr Ser Ile Pro Ser Ser Gly Lys Ile Ala Lys Asp Ala Lys Glu
                 20                  25                  30

Cys Val Gln Glu Cys Val Ser Glu Phe Ile Ser Phe Ile Thr Ser Glu
            35                  40                  45

Ala Ser Glu Arg Cys His Gln Glu Lys Arg Lys Thr Ile Asn Gly Glu
 50                  55                  60

Asp Ile Leu Phe Ala Met Ser Thr Leu Gly Phe Gln Ser Tyr Val Glu
 65                  70                  75                  80

Pro Leu Lys Gln Tyr Leu Gln Lys Tyr Arg
                 85                  90

<210> SEQ ID NO 23
<211> LENGTH: 57
<212> TYPE: PRT
<213> ORGANISM: Xenopus laevis
```

```
<220> FEATURE:
<221> NAME/KEY: DOMAIN
<222> LOCATION: (1)..(57)
<223> OTHER INFORMATION: Xenopus HAP3 subunit of CCAAT box-binding
      factor (CBF) protein B domain homolog

<400> SEQUENCE: 23

Val Gln Glu Cys Val Ser Glu Phe Ile Ser Phe Ile Thr Ser Glu Ala
 1               5                  10                  15

Ser Glu Arg Cys His Gln Glu Lys Arg Lys Thr Ile Asn Gly Glu Asp
                20                  25                  30

Ile Leu Phe Ala Met Ser Thr Leu Gly Phe Gln Ser Tyr Val Glu Pro
            35                  40                  45

Leu Lys Leu Tyr Leu Gln Lys Phe Arg
        50                  55

<210> SEQ ID NO 24
<211> LENGTH: 90
<212> TYPE: PRT
<213> ORGANISM: Homo sapiens
<220> FEATURE:
<221> NAME/KEY: DOMAIN
<222> LOCATION: (1)..(90)
<223> OTHER INFORMATION: human HAP3 subunit of CCAAT Box-binding factor
      (CBF) protein B domain homolog

<400> SEQUENCE: 24

Arg Glu Gln Asp Ile Tyr Leu Pro Ile Ala Asn Val Ala Arg Ile Met
 1               5                  10                  15

Lys Asn Ala Ile Pro Gln Thr Gly Lys Ile Ala Lys Asp Ala Lys Glu
                20                  25                  30

Cys Val Gln Glu Cys Val Ser Glu Phe Ile Ser Phe Ile Thr Ser Glu
            35                  40                  45

Ala Ser Glu Arg Cys His Gln Glu Lys Arg Lys Thr Ile Asn Gly Glu
        50                  55                  60

Asp Ile Leu Phe Ala Met Ser Thr Leu Gly Phe Gln Ser Tyr Val Glu
65                  70                  75                  80

Pro Leu Lys Leu Tyr Leu Gln Lys Phe Arg
                85                  90

<210> SEQ ID NO 25
<211> LENGTH: 90
<212> TYPE: PRT
<213> ORGANISM: Mus musculus and Rattus norvegicus
<220> FEATURE:
<221> NAME/KEY: DOMAIN
<222> LOCATION: (1)..(90)
<223> OTHER INFORMATION: mouse/rat HAP3 subunit of CCAAT box-binding
      factor (CBF) protein B domain homolog

<400> SEQUENCE: 25

Arg Glu Gln Asp Ile Tyr Leu Pro Ile Ala Asn Val Ala Arg Ile Met
 1               5                  10                  15

Lys Asn Ala Ile Pro Gln Thr Gly Lys Ile Ala Lys Asp Ala Lys Glu
                20                  25                  30

Cys Val Gln Glu Cys Val Ser Glu Phe Ile Ser Phe Ile Thr Ser Glu
            35                  40                  45

Ala Ser Glu Arg Cys His Gln Glu Lys Arg Lys Thr Ile Asn Gly Glu
        50                  55                  60

Asp Ile Leu Phe Ala Met Ser Thr Leu Gly Phe Gln Ser Tyr Val Glu
65                  70                  75                  80
```

```
Pro Leu Lys Leu Tyr Leu Gln Lys Phe Arg
            85                  90
```

<210> SEQ ID NO 26
<211> LENGTH: 90
<212> TYPE: PRT
<213> ORGANISM: Emericella nidulans
<220> FEATURE:
<221> NAME/KEY: DOMAIN
<222> LOCATION: (1)..(90)
<223> OTHER INFORMATION: E. nidulans HAP3 subunit of CCAAT box-binding
      factor (CBF) protein B domain homolog

<400> SEQUENCE: 26

```
Lys Glu Gln Asp Arg Trp Leu Pro Ile Ala Asn Val Ala Arg Ile Met
  1               5                  10                  15

Lys Leu Ala Leu Pro Glu Asn Ala Lys Ile Ala Lys Glu Ala Lys Glu
                 20                  25                  30

Cys Met Gln Glu Cys Val Ser Glu Phe Ile Ser Phe Ile Thr Ser Glu
             35                  40                  45

Ala Ser Glu Lys Cys Gln Gln Glu Lys Arg Lys Thr Val Asn Gly Glu
         50                  55                  60

Asp Ile Leu Phe Ala Met Thr Ser Leu Gly Phe Glu Asn Tyr Ala Glu
 65                  70                  75                  80

Ala Leu Lys Ile Tyr Leu Ser Lys Tyr Arg
                 85                  90
```

<210> SEQ ID NO 27
<211> LENGTH: 85
<212> TYPE: PRT
<213> ORGANISM: Schizosaccharomyces pombe
<220> FEATURE:
<221> NAME/KEY: DOMAIN
<222> LOCATION: (1)..(85)
<223> OTHER INFORMATION: S. pombe HAP3 subunit of CCAAT box-binding
      factor (CBF) protein B domain homolog

<400> SEQUENCE: 27

```
Leu Leu Pro Ile Ala Asn Val Ala Arg Ile Met Lys Ser Ala Leu Pro
  1               5                  10                  15

Glu Asn Ala Lys Ile Ser Lys Glu Ala Lys Asp Cys Val Gln Asp Cys
                 20                  25                  30

Val Ser Glu Phe Ile Ser Phe Val Thr Gly Glu Ala Ser Glu Gln Cys
             35                  40                  45

Thr Gln Glu Lys Arg Lys Thr Ile Thr Gly Glu Asp Val Leu Leu Ala
         50                  55                  60

Leu Asn Thr Leu Gly Phe Glu Asn Tyr Ala Glu Val Leu Lys Ile Ser
 65                  70                  75                  80

Leu Thr Lys Tyr Arg
                 85
```

<210> SEQ ID NO 28
<211> LENGTH: 90
<212> TYPE: PRT
<213> ORGANISM: Saccharomyces cerevisiae
<220> FEATURE:
<221> NAME/KEY: DOMAIN
<222> LOCATION: (1)..(90)
<223> OTHER INFORMATION: S. cerevisiae HAP3 subunit of CCAAT box-binding
      factor (CBF) protein B domain homolog

<400> SEQUENCE: 28

```
Arg Glu Gln Asp Arg Trp Leu Pro Ile Asn Asn Val Ala Arg Leu Met
```

-continued

```
                1               5                      10                      15
Lys Asn Thr Leu Pro Pro Ser Ala Lys Val Ser Lys Asp Ala Lys Glu
                        20                      25                      30

Cys Met Gln Glu Cys Val Ser Glu Leu Ile Ser Phe Val Thr Ser Glu
                35                      40                      45

Ala Ser Asp Arg Cys Ala Ala Asp Lys Arg Lys Thr Ile Asn Gly Glu
        50                      55                      60

Asp Ile Leu Ile Ser Leu His Ala Leu Gly Phe Glu Asn Tyr Ala Glu
 65                     70                      75                      80

Val Leu Lys Ile Tyr Leu Ala Lys Tyr Arg
                85                      90

<210> SEQ ID NO 29
<211> LENGTH: 90
<212> TYPE: PRT
<213> ORGANISM: Kluyveromyces lactis
<220> FEATURE:
<221> NAME/KEY: DOMAIN
<222> LOCATION: (1)..(90)
<223> OTHER INFORMATION: K. lactis HAP3 subunit of CCAAT box-binding
      factor (CBF) protein B domain homolog

<400> SEQUENCE: 29

Ala Glu Gln Asp Arg Trp Leu Pro Ile Asn Asn Val Ala Arg Leu Met
 1               5                      10                      15

Lys Asn Thr Leu Pro Ala Thr Thr Lys Val Ser Lys Asp Ala Lys Glu
                        20                      25                      30

Cys Met Gln Glu Cys Val Ser Glu Phe Ile Ser Phe Val Thr Ser Glu
                35                      40                      45

Ala Cys Asp Arg Cys Thr Ser Gly Lys Arg Lys Thr Ile Asn Gly Glu
        50                      55                      60

Asp Ile Leu Leu Ser Leu His Ala Leu Gly Phe Glu Asn Tyr Ala Glu
 65                     70                      75                      80

Val Leu Lys Ile Tyr Leu Ala Lys Tyr Arg
                85                      90
```

LEAFY COTYLEDON1 GENES AND THEIR USES

CROSS REFERENCE TO RELATED APPLICATIONS

The present application is a Continuation-In-Part ("CIP") of U.S. patent application Ser. No. 09/103,478, filed Jun. 24, 1998 now U.S. Pat. No. 6,235,975 which is a CIP of U.S. Ser. No. 09/026,221, filed Feb. 19, 1998, which is a CIP of U.S. Ser. No. 08/804,534, filed Feb. 21, 1997 now abandoned. Each of the aforementioned applications is explicitly incorporated herein by reference in their entirety and for all purposes.

FIELD OF THE INVENTION

The present invention is directed to plant genetic engineering. In particular, it relates to new embryo-specific genes useful in improving agronomically important plants.

BACKGROUND OF THE INVENTION

Embryogenesis in higher plants is a critical stage of the plant life cycle in which the primary organs are established. Embryo development can be separated into two main phases: the early phase in which the primary body organization of the embryo is laid down and the late phase which involves maturation, desiccation and dormancy. In the early phase, the symmetry of the embryo changes from radial to bilateral, giving rise to a hypocotyl with a shoot meristem surrounded by the two cotyledonary primordia at the apical pole and a root meristem at the basal pole. In the late phase, during maturation the embryo achieves its maximum size and the seed accumulates storage proteins and lipids. Maturation is ended by the desiccation stage in which the seed water content decreases rapidly and the embryo passes into metabolic quiescent state. Dormancy ends with seed germination, and development continues from the shoot and the root meristem regions.

The precise regulatory mechanisms which control cell and organ differentiation during the initial phase of embryogenesis are largely unknown. The plant hormone abscisic acid (ABA) is thought to play a role during late embryogenesis, mainly in the maturation stage by inhibiting germination during embryogenesis (Black, M. (1991). In Abscisic Acid: Physiology and Biochemistry, W. J. Davies and H. G. Jones, eds. (Oxford: Bios Scientific Publishers Ltd.), pp. 99–124) Koornneef, M., and Karssen, C. M. (1994). In Arabidopsis, E. M. Meyerowitz and C. R. Sommerville, eds. (Cold Spring Harbor: Cold Spring Harbor Laboratory Press), pp. 313–334). Mutations which effect seed development and are ABA insensitive have been identified in Arabidopsis and maize. The ABA insensitive (abi3) mutant of Arabidopsis and the viviparous1 (vp1) mutant of maize are detected mainly during late embryogenesis (McCarty, et al., (1989) Plant Cell 1, 523–532 and Parcy et al., (1994) Plant Cell 6, 1567–1582). Both the VP1 gene and the ABI3 genes have been isolated and were found to share conserved regions (Giraudat, J. (1995) Current Opinion in Cell Biology 7:232–238 and McCarty, D. R. (1995). Annu. Rev. Plant Physiol. Plant Mol. Biol. 46:71–93). The VP1 gene has been shown to function as a transcription activator (McCarty, et al., (1991) Cell 66:895–906). It has been suggested that ABI3 has a similar function.

Another class of embryo defective mutants involves three genes: LEAFY COTYLEDON1 and 2 (LEC1, LEC2) and FUSCA3 (FUS3). These genes are thought to play a central role in late embryogenesis (Baumnlein, et al. (1994) Plant J. 6:379–387; Meinke, D. W. (1992) Science 258:1647–1650; Meinke et al., Plant Cell 6:1049–1064; West et al., (1994) Plant Cell 6:1731–1745). Like the abi3 mutant, leafy cotyledon-type mutants are defective in late embryogenesis. In these mutants, seed morphology is altered, the shoot meristem is activated early, storage proteins are lacking and developing cotyledons accumulate anthocyanin. As with abi3 mutants, they are desiccation intolerant and therefore die during late embryogenesis. Nevertheless, the immature mutants embryos can be rescued to give rise to mature and fertile plants. However, unlike abi3 when the immature mutants germinate they exhibit trichomes on the adaxial surface of the cotyledon. Trichomes are normally present only on leaves, stems and sepals, not cotyledons. Therefore, it is thought that the leafy cotyledon type genes have a role in specifying cotyledon identity during embryo development.

Among the above mutants, the lec1 mutant exhibits the most extreme phenotype during embryogenesis. For example, the maturation and postgermination programs are active simultaneously in the lec1 mutant (West et al., 1994), suggesting a critical role for LEC1 in gene regulation during late embryogenesis.

In spite of the recent progress in defining the genetic control of embryo development, further progress is required in the identification and analysis of genes expressed specifically in the embryo and seed. Characterization of such genes would allow for the genetic engineering plants with a variety of desirable traits. For instance, modulation of the expression of genes which control embryo development may be used to alter traits such as accumulation of storage proteins in leaves and cotyledons. Alternatively, promoters from embryo or seed-specific genes can be used to direct expression of desirable heterologous genes to the embryo or seed. The present invention addresses these and other needs.

SUMMARY OF THE INVENTION

The present invention is based, in part, on the isolation and characterization of LEC1 genes. The invention provides isolated nucleic acid molecules comprising a LEC1 polynucleotide sequence, typically about 630 nucleotides in length, which specifically hybridizes to SEQ ID NO:1 under stringent conditions. The LEC1 polynucleotides of the invention can encode a LEC1 polypeptide of about 210 amino acids, typically as shown in SEQ ID NO:2.

The invention provides an isolated nucleic acid molecule comprising a LEC1 polynucleotide sequence, the polynucleotide sequence defined as follows: the polynucleotide sequence specifically hybridizes to SEQ ID NO:1 under stringent conditions; or the polynucleotide sequence has at least 70% sequence identity to SEQ ID NO:1. In alternative embodiments, the isolated nucleic acid molecule of can have at least 75% sequence identity, at least 80% sequence identity, at least 85% sequence identity, at least 90% sequence identity, at least 95% sequence identity to SEQ ID NO:1; and, the isolated nucleic acid molecule can have the sequence set forth in SEQ ID NO:1.

In different embodiments, the isolated nucleic acid molecule of the invention is a LEC1 polynucleotide between about 100 nucleotides and about 630 nucleotides in length, and, between about 50 and about 210 amino acids in length. The isolated nucleic acid molecule of the invention can encode a LEC1 polypeptide having an amino acid sequence as shown in SEQ ID NO:2.

The invention also provides an isolated LEC1 nucleic acid molecule further comprising an operably linked promoter. In alternative embodiments, the promoter is a constitutive promoter, where the constitutive promoter is a cauliflower mosaic virus (CaMV) 35S transcription initiation region or a 1'- or 2'- promoter derived from T-DNA of Agrobacterium tumafaciens, and the promoter is an inducible promoter. The promoter can also be a plant promoter. In various embodiments, the plant promoter is a tissue-specific promoter and is a tissue-specific promoter active in vegetative tissue or reproductive tissue. The plant promoter can be from a LEC1 gene, where LEC1 gene can be as shown in SEQ ID NO:3. In different embodiments, the plant promoter can be from about nucleotide 1 to about nucleotide 1998 of SEQ ID NO:3, or, the promoter can be from the LEC1 gene is as shown in SEQ ID NO:4. The LEC1 polynucleotide can be linked to the promoter in an antisense orientation.

The invention also provides LEC1 polynucleotide further comprising an expression vector, an expression cassette, or a plant virus.

The invention further provides an isolated nucleic acid molecule comprising a LEC1 polynucleotide sequence, wherein the polynucleotide sequence specifically hybridizes to SEQ ID NO:1 under stringent conditions, or (b) the polynucleotide sequence has at least 70% sequence identity to SEQ ID NO:1, and, (ii) wherein the polynucleotide sequence encodes a LEC1 polypeptide of between about 50 and about 210 amino acids. The LEC1 polypeptide can have an amino acid sequence as shown in SEQ ID NO:2. In alternative embodiments, the polynucleotide sequence can have at least 75% sequence identity, at least 80% sequence identity, at least 85% sequence identity, at least 90% sequence identity, at least 95% sequence identity to SEQ ID NO:1; and, the polynucleotide sequence can have the sequence set forth in SEQ ID NO:1.

The invention provides a transgenic plant comprising a heterologous LEC1 polynucleotide operably linked to a promoter, the LEC1 polynucleotide sequence defined as follows: the polynucleotide sequence specifically hybridizes to SEQ ID NO:1 under stringent conditions; or the polynucleotide sequence has at least 70% sequence identity to SEQ ID NO:1. In alternative embodiments, the polynucleotide sequence can have at least 75% sequence identity, at least 80% sequence identity, at least 85% sequence identity, at least 90% sequence identity, at least 95% sequence identity to SEQ ID NO:1; and, the polynucleotide sequence can have the sequence set forth in SEQ ID NO:1. The heterologous LEC1 polynucleotide can encode a LEC1 polypeptide. The LEC1 polypeptide can be SEQ ID NO:2. In the transgenic plant, the heterologous LEC1 polynucleotide can be linked to the promoter in an antisense orientation. The promoter can be from a LEC1 gene. The LEC1 gene can have the sequence as shown in SEQ ID NO:3. The transgenic plant can be a member of the genus Brassica.

The invention provides an isolated LEC1 polypeptide comprising a polypeptide sequence defined as follows: (i) the polypeptide sequence is encoded by a polynucleotide sequence which specifically hybridizes to SEQ ID NO:1 under stringent conditions, or (i) the polypeptide sequence is encoded by a polynucleotide sequence having at least 70% sequence identity to SEQ ID NO:1, or (ii) the polypeptide sequence has at least 50% sequence identity to SEQ ID NO:2. In alternative embodiments, the polynucleotide sequence can have at least 75% sequence identity, at least 80% sequence identity, at least 85% sequence identity, at least 90% sequence identity, at least 95% sequence identity to SEQ ID NO:1; and, the polynucleotide sequence can have the sequence set forth in SEQ ID NO:1. In alternative embodiments, the isolated LEC1 polypeptide can have at least 60% sequence identity, at least 70% sequence identity, at least 80% sequence identity, at least 90% sequence identity, and at least 95% sequence identity to SEQ ID NO:2. The isolated LEC1 polypeptide can have the sequence set forth in SEQ ID NO:2.

The invention also provides a method of modulating seed development in a plant, the method comprising introducing into the plant a heterologous LEC1 polynucleotide operably linked to a promoter, wherein the LEC1 polynucleotide has a sequence defined as follows: the polynucleotide sequence specifically hybridizes to SEQ ID NO:1 under stringent conditions; or the polynucleotide sequence has at least 70% sequence identity to SEQ ID NO:1. In alternative embodiments, the polynucleotide sequence can have at least 75% sequence identity, at least 80% sequence identity, at least 85% sequence identity, at least 90% sequence identity, at least 95% sequence identity to SEQ ID NO:1; and, the polynucleotide sequence can have the sequence set forth in SEQ ID NO:1.

In this method, the heterologous LEC1 polynucleotide can encode a LEC1 polypeptide. The LEC1 polypeptide can have an amino acid sequence as shown in SEQ ID NO:2. The heterologous LEC1 polynucleotide can be linked to the promoter in an antisense orientation. In this method, the heterologous LEC1 polynucleotide can be SEQ ID NO:1. The promoter can be from a LEC1 gene. The method LEC1 gene can be a sequence as shown in SEQ ID NO:3. The plant can be a member of the genus Brassica. The heterologous LEC1 polynucleotide can be introduced into the plant through a sexual cross. In this method, the heterologous LEC1 polynucleotide can be co-expressed with a second heterologous polynucleotide. The second heterologous nucleotide can be selected from the group consisting of AP2 and RAP2 genes of Arabidopsis, and the second heterologous polynucleotide can be expressed in the antisense orientation.

The invention further provides a method of inducing ectopic development of embryonic tissue in a plant, the method comprising introducing into the plant a heterologous LEC1 polynucleotide operably linked to a promoter, wherein the LEC1 polynucleotide has a sequence defined as follows: the polynucleotide sequence specifically hybridizes to SEQ ID NO:1 under stringent conditions; or the polynucleotide sequence has at least 70% sequence identity to SEQ ID NO:1. In alternative embodiments, the polynucleotide sequence can have at least 75% sequence identity, at least 80% sequence identity, at least 85% sequence identity, at least 90% sequence identity, at least 95% sequence identity to SEQ ID NO:1; and, the polynucleotide sequence can have the sequence set forth in SEQ ID NO:1. In this method, the heterologous LEC1 polynucleotide can be co-expressed with a second heterologous polynucleotide. The second heterologous nucleotide can be selected from the group consisting of AP2 and RAP2 genes of Arabidopsis, and the second heterologous nucleotide can be expressed in the antisense orientation.

The invention provides an isolated nucleic acid molecule comprising a plant promoter that specifically hybridizes to a polynucleotide sequence consisting of nucleotides 1 to 1998 of SEQ ID NO:3. The plant promoter sequence can consist essentially of about nucleotides 1 to about 1998 of SEQ ID NO:3, or it can be a subsequence of SEQ ID NO:4. In one embodiment, a polynucleotide sequence can be operably linked to the plant promoter of the invention. The polynucleotide sequence operably linked to the plant promoter can encode a polypeptide, and this polynucleotide sequence can linked to the promoter in an antisense orientation.

The invention also provides a transgenic plant comprising a LEC1 promoter operably linked to a heterologous polynucleotide sequence, wherein the LEC1 promoter has a polynucleotide sequence defined as follows: the polynucleotide sequence specifically hybridizes to SEQ ID NO:3 under stringent conditions; or the polynucleotide sequence specifically hybridizes to SEQ ID NO:4 under stringent conditions. In alternative embodiments, the heterologous polynucleotide sequence encodes a desired polypeptide, and the heterologous polynucleotide sequence is linked to the LEC1 promoter in an antisense orientation. The LEC1 promoter can have the sequence shown in SEQ ID NO:3 or SEQ ID NO:4. The heterologous polynucleotide sequence can be linked to the LEC1 promoter in an antisense orientation. The transgenic plant can be a member of the genus Brassica.

The invention further provides a method of targeting expression of a polynucleotide to a seed, the method comprising introducing into a plant a LEC1 promoter operably linked to a heterologous polynucleotide sequence, wherein the LEC1 promoter specifically hybridizes to a polynucleotide sequence consisting of nucleotides 1 to 1998 of SEQ ID NO:3. In this method, the heterologous polynucleotide sequence can encode a desired polypeptide. The heterologous polynucleotide sequence can be linked to the promoter in an antisense orientation.

Definitions

The phrase "nucleic acid" refers to a single or double-stranded polymer of deoxyribonucleotide or ribonucleotide bases read from the 5' to the 3' end. Nucleic acids may also include modified nucleotides that permit correct read through by a polymerase and do not alter expression of a polypeptide encoded by that nucleic acid.

The phrase "polynucleotide sequence" or "nucleic acid sequence" includes both the sense and antisense strands of a nucleic acid as either individual single strands or in the duplex. It includes, but is not limited to, self-replicating plasmids, chromosomal sequences, and infectious polymers of DNA or RNA.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

The term "promoter" refers to a region or sequence determinants located upstream or downstream from the start of transcription and which are involved in recognition and binding of RNA polymerase and other proteins to initiate transcription. A "plant promoter" is a promoter capable of initiating transcription in plant cells. Such promoters need not be of plant origin, for example, promoters derived from plant viruses, such as the CaMV35S promoter, can be used in the present invention.

The term "plant" includes whole plants, plant organs (e.g., leaves, stems, flowers, roots, etc.), seeds and plant cells and progeny of same. The class of plants which can be used in the method of the invention is generally as broad as the class of higher plants amenable to transformation techniques, including both monocotyledonous and dicotyledonous plants, as well as certain lower plants such as algae. It includes plants of a variety of ploidy levels, including polyploid, diploid and haploid.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants. As defined here, a modified LEC1 coding sequence which is heterologous to an operably linked LEC1 promoter does not include the T-DNA insertional mutants as described in West et al., The Plant Cell 6:1731–1745 (1994).

A polynucleotide "exogenous to" an individual plant is a polynucleotide which is introduced into the plant by any means other than by a sexual cross. Examples of means by which this can be accomplished are described below, and include Agrobacterium-mediated transformation, biolistic methods, electroporation, in planta techniques, and the like. Such a plant containing the exogenous nucleic acid is referred to here as an $R_1$ generation transgenic plant. Transgenic plants which arise from sexual cross or by selfing are descendants of such a plant.

As used herein an "embryo-specific gene" or "seed specific gene" is a gene that is preferentially expressed during embryo development in a plant. For purposes of this disclosure, embryo development begins with the first cell divisions in the zygote and continues through the late phase of embryo development (characterized by maturation, desiccation, dormancy), and ends with the production of a mature and desiccated seed. Embryo-specific genes can be further classified as "early phase-specific" and "late phase-specific". Early phase-specific genes are those expressed in embryos up to the end of embryo morphogenesis. Late phase-specific genes are those expressed from maturation through to production of a mature and desiccated seed.

A "LEC1 polynucleotide" is a nucleic acid sequence comprising (or consisting of) a coding region of about 100 to about 900 nucleotides, sometimes from about 300 to about 630 nucleotides, which hybridizes to SEQ ID NO:1 under stringent conditions (as defined below), or which encodes a LEC1 polypeptide. LEC1 polynucleotides can also be identified by their ability to hybridize under low stringency conditions (e.g., Tm −40° C.) to nucleic acid probes having a sequence from position 1 to 81 in SEQ ID NO:1 or from position 355 to 627 in SEQ ID NO:1.

A "promoter from a LEC1 gene" or "LEC1 promoter" will typically be about 500 to about 2000 nucleotides in length, usually from about 750 to 1500. An exemplary promoter sequence is shown as nucleotides 1–1998 of SEQ ID NO:3. A LEC1 promoter can also be identified by its ability to direct expression in all, or essentially all, proglobular embryonic cells, as well as cotyledons and axes of a late embryo.

A "LEC1 polypeptide" is a sequence of about 50 to about 210, sometimes 100 to 150, amino acid residues encoded by a LEC1 polynucleotide. A full length LEC1 polypeptide and fragments containing a CCAAT binding factor (CBF) domain can act as a subunit of a protein capable of acting as a transcription factor in plant cells. LEC1 polypeptides are often distinguished by the presence of a sequence which is required for binding the nucleotide sequence: CCAAT. In particular, a short region of seven residues (MPIANVI; SEQ ID NO:5) at residues 34–40 of SEQ ID NO:2 shows a high degree of similarity to a region that has been shown to required for binding the CCAAT box. Similarly, residues 61–72 of SEQ ID NO:2 (IQECVSEYISFV; SEQ ID NO:6 ) is nearly identical to a region that contains a subunit interaction domain (Xing, et al., (1993) EMBO J. 12:4647–4655).

As used herein, a homolog of a particular embryo-specific gene (e.g., SEQ ID NO:1) is a second gene in the same plant type or in a different plant type, which has a polynucleotide sequence of at least 50 contiguous nucleotides which are substantially identical (determined as described below) to a sequence in the first gene. It is believed that, in general, homologs share a common evolutionary past.

A "polynucleotide sequence from" a particular embryo-specific gene is a subsequence or fill length polynucleotide sequence of an embryo-specific gene which, when present in a transgenic plant, has the desired effect, for example, inhibiting expression of the endogenous gene driving expression of an heterologous polynucleotide. A full length sequence of a particular gene disclosed here may contain about 95%, usually at least about 98% of an entire sequence shown in the Sequence Listing, below.

The term "reproductive tissues" as used herein includes fruit, ovules, seeds, pollen, pistols, flowers, or any embryonic tissue.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the term "polynucleotide sequence from" a particular embryo-specific gene, such as LEC1. In addition, the term specifically includes sequences (e.g., full length sequences) substantially identical (determined as described below) with a LEC1 gene sequence and that encode proteins that retain the function of a LEC1 polypeptide.

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman Add. APL. Math. 2:482 (1981), by the homology alignment algorithm of Needle man and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 70% sequence identity, at least 80% sequence identity, preferably at least 85%, more preferably at least 90% and most preferably at least 95%, compared to a reference sequence using the programs described herein; preferably BLAST using standard parameters, as described below. Accordingly, LEC1 sequences of the invention include nucleic acid sequences that have substantial identity to SEQ ID NO:1, SEQ ID NO:3 and SEQ ID NO:4. LEC1 sequences of the invention include polypeptide sequences having substantial identify to SEQ ID NO:2. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

In the present invention, mRNA encoded by embryo-specific genes of the invention can be identified in Northern blots under stringent conditions using cDNAs of the invention or fragments of at least about 100 nucleotides. For the purposes of this disclosure, stringent conditions for such RNA-DNA hybridizations are those which include at least one wash in 0.2×SSC at 63° C. for 20 minutes, or equivalent conditions. Genomic DNA or cDNA comprising genes of the invention can be identified using the same cDNAs (or fragments of at least about 100 nucleotides) under stringent conditions, which for purposes of this disclosure, include at least one wash (usually 2) in 0.2×SSC at a temperature of at least about 50° C., usually about 55° C., for 20 minutes, or equivalent conditions.

DESCRIPTION OF THE PREFERRED EMBODIMENT

Figure 1:
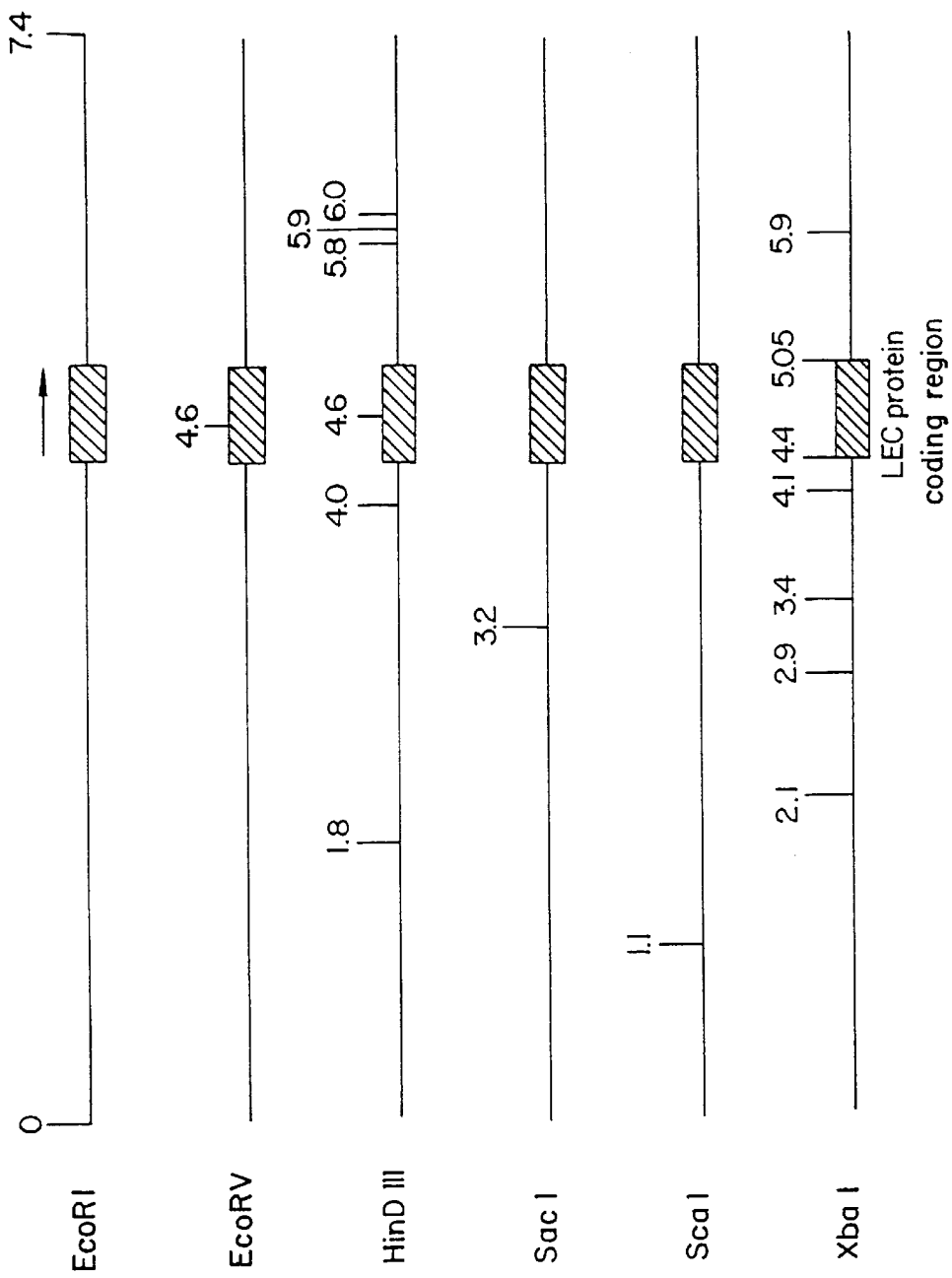
FIG. 1 is a restriction map of the 7.4 kb genomic wild-type fragment shown in SEQ ID NO:4.

The present invention provides new embryo-specific genes useful in genetically engineering plants. Polynucleotide sequences from the genes of the invention can be used, for instance, to direct expression of desired heterologous genes in embryos (in the case of promoter sequences) or to modulate development of embryos or other organs (e.g., by enhancing expression of the gene in a transgenic plant). In particular, the invention provides a new gene from Arabidopsis referred to here as LEC1. LEC1 encodes polypeptides which subunits of a protein which acts as a transcription factor. Thus, modulation of the expression of this gene can be used to manipulate a number of useful traits, such as increasing or decreasing storage protein content in cotyledons or leaves.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, 2nd. ed., Cold Spring Harbor Laboratory, Cold Spring Harbor, N.Y., (1989).

Isolation of Nucleic Acids of the Invention

The isolation of sequences from the genes of the invention may be accomplished by a number of techniques. For instance, oligonucleotide probes based on the sequences disclosed here can be used to identify the desired gene in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. To prepare a library of embryo-specific cDNAs, mRNA is isolated from embryos and a cDNA library which contains the gene transcripts is prepared from the mRNA.

The cDNA or genomic library can then be screened using a probe based upon the sequence of a cloned embryo-specific gene such as the polynucleotides disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying embryo-specific genes from plant tissues are generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990). Appropriate primers for this purpose include, for instance: UP primer-5' GGA ATT CAG CAA CAA CCC AAC CCC A 3' (SEQ ID NO:7) and LP primer-5' GCT CTA GAC ATA CAA CAC TTT TCC TTA 3' (SEQ ID NO:8). Alternatively, the following primer pairs can be used: 5' ATG ACC AGC TCA GTC ATA GTA GC 3' (SEQ ID NO:9) and 5' GCC ACA CAT GGT GGT TGC TGC TG 3' (SEQ ID NO:10) or 5' GAG ATA GAG ACC GAT CGT GGT TC 3' (SEQ ID NO:11) and 5' TCA CTT ATA CTG ACC ATA ATG GTC 3' (SEQ ID NO:12). The amplifications conditions are typically as follows. Reaction components: 10 mM Tris-HCl, pH 8.3, 50 mM potassium chloride, 1.5 mM magnesium chloride, 0.001% gelatin, 200 microM (uM) dATP, 200 microM dCTP, 200 microM dGTP, 200 microM dTTP, 0.4 microM primers, and 100 units per ml Taq polymerase. Program: 96 C. for 3 min., 30 cycles of 96 C. for 45 sec., 50 C. for 60 sec., 72 for 60 sec, followed by 72 C. for 5 min.

Polynucleotides may also be synthesized by well-known techniques as described in the technical literature. See, e.g., Carruthers et al., Cold Spring Harbor Symp. Quant. Biol. 47:411–418 (1982), and Adams et al., J. Am. Chem. Soc. 105:661 (1983). Double stranded DNA fragments may then be obtained either by synthesizing the complementary strand and annealing the strands together under appropriate conditions, or by adding the complementary strand using DNA polymerase with an appropriate primer sequence.

Analysis of LEC1 Gene Sequences

The genus of LEC1 nucleic acid sequences of the invention includes genes and gene products identified and characterized by analysis using the sequences nucleic acid sequences, including SEQ ID NO:1, SEQ ID NO:3 and SEQ ID NO:4, and protein sequences, including SEQ ID NO:2.

LEC1 sequences of the invention include nucleic acid sequences having substantial identity to SEQ ID NO:1, SEQ ID NO:3 and SEQ ID NO:4. LEC1 sequences of the invention include polypeptide sequences having substantial identify to SEQ ID NO:2. "Substantial identity" of a sequence means that it comprises a sequence that has at least 70% sequence identity, at least 80% sequence identity, preferably at least 85%, more preferably at least 90% and most preferably at least 95%, compared to a reference sequence using the programs described herein.

Optimal alignment of sequences for comparison can use any means to analyze sequence identity (homology) known in the art, e.g., by the progressive alignment method of termed "PILEUP" (see below); by the local homology algorithm of Smith & Waterman (1981) Adv. Appl. Math. 2: 482; by the homology alignment algorithm of Needleman & Wunsch (1970) J. Mol. Biol. 48:443; by the search for similarity method of Pearson (1988) Proc. Natl. Acad. Sci. USA 85: 2444; by computerized implementations of these algorithms (e.g., GAP, BESTFIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins (1988) Gene 73: 237–244; Corpet (1988) Nucleic Acids Res. 16:10881–90; Huang (1992) Computer Applications in the Biosciences 8:155–65, and Pearson (1994) Methods in Molec. Biol. 24:307–31), Pfam (Sonnhammer (1998) Nucleic Acids Res. 26:322–325); TreeAlign (Hein (1994) Methods Mol. Biol. 25:349–364; MES-ALIGN, and SAM sequence alignment computer programs; or, by inspection. See also Morrison (1997) Mol. Biol. Evol. 14:428–441, as an example of the use of PILEUP.

Another example of algorithm that is suitable for determining sequence similarity is the BLAST algorithm, which is described in Altschul (1990) J. Mol. Biol. 215: 403–410. Software for performing BLAST analyses is publicly available through the National Center for Biotechnology Information, http://www.ncbi.nlm.nih.gov/; see also Zhang (1997) Genome Res. 7:649–656 (1997) for the "Power-BLAST"variation. This algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold (Altschul et al, supra.). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a wordlength (W) of 11, the BLOSUM62 scoring matrix (see Henikoff (1992) Proc. Natl. Acad. Sci. USA 89: 10915–10919) alignments (B) of 50, expectation (E) of 10, M=5, N=−4, and a comparison of both strands. The term BLAST refers to the BLAST algorithm which performs a statistical analysis of the similarity between two sequences; see, e.g., Karlin (1993) Proc. Natl. Acad. Sci. USA 90:5873–5787. One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Use of Nucleic Acids of the Invention to Inhibit Gene Expression

The isolated sequences prepared as described herein, can be used to prepare expression cassettes useful in a number of techniques. For example, expression cassettes of the invention can be used to suppress endogenous LEC1 gene expression. Inhibiting expression can be useful, for instance, in weed control (by transferring an inhibitory sequence to a weedy species and allowing it to be transmitted through sexual crosses) or to produce fruit with small and non-viable seed.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., Proc. Nat. Acad. Sci. USA, 85:8805–8809 (1988), and Hiatt et al., U.S. Pat. No. 4,801,340.

The nucleic acid segment to be introduced generally will be substantially identical to at least a portion of the endogenous embryo-specific gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of embryo-specific genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. Nature, 334:585–591 (1988).

Another method of suppression is sense suppression. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., The Plant Cell 2:279–289 (1990), and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Another means of inhibiting LEC1 function in a plant is by creation of dominant negatives. In this approach, non-functional, mutant LEC1 polypeptides, which retain the ability to interact with wild-type subunits are introduced into a plant. Identification of residues that can be changed to create a dominant negative can be determined by published work examining interaction of different subunits of CBF homologs from different species (see, e.g., Sinha et al., (1995). Proc. Natl. Acad. Sci. USA 92:1624–1628.)

Use of Nucleic Acids of the Invention to Enhance Gene Expression

Isolated sequences prepared as described herein can also be used to prepare expression cassettes which enhance or increase endogenous LEC1 gene expression. Where overexpression of a gene is desired, the desired gene from a different species may be used to decrease potential sense suppression effects. Enhanced expression of LEC1 polynucleotides is useful, for example, to increase storage protein content in plant tissues. Such techniques may be particularly useful for improving the nutritional value of plant tissues.

Figure 2:
FIG. 2A show a schematic representation of the three domains of the LEC1 polypeptide.
FIG. 2B shows a comparison of the predicted amino acid sequence of the B domain encoded by LEC1 (SEQ ID NO:19) with HAP3 homologs from maize (SEQ ID NO:20), chicken (SEQ ID NO:21), lamprey (SEQ ID NO:22), *Xenopus laevis* (SEQ ID NO:23), human (SEQ ID NO:24), mouse/rat (SEQ ID NO:25), *Emericella nidulans* (SEQ ID NO:26), *Schizosaccharomyces pombe* (SEQ ID NO:27), *Saccharomyces cerevsiae* (SEQ ID NO:28), and *Kluyveromyces lactis* (SEQ ID NO:29). The DNA-binding region and the subunit interaction region are indicated. Numbers indicate amino acid positions of the B domains.

One of skill will recognize that the polypeptides encoded by the genes of the invention, like other proteins, have different domains which perform different functions. Thus, the gene sequences need not be full length, so long as the desired functional domain of the protein is expressed. As explained above, LEC1 polypeptides are related to CCAAT box-binding factor (CBF) proteins. CBFs are highly conserved family of transcription factors that regulate gene activity in eukaryotic organisms (see, e.g,, Mantvani (1992) Nucl. Acids Res. 20:1087–1091; Li (1992) Nucleic Acids Res. 20:1087–1091). LEC1 was found to have high similarity to a portion of the HAP3 subunit of CBF. HAP3 is divided into three domains, an amino terminal A domain, a central B domain, and a carboxyl terminal C domain, as shown diagrammatically in FIG. 2A. Specifically, LEC1, has between about 75% and 85% sequence similarity, which is equivalent to 55% to 63% sequence identity, with the B domains of the other HAP3 homologs shown in FIG. 2B; see also, Example 1, below. FIG. 2B shows the amino acid sequence homology between LEC1 and other CBF homologs.

The LEC1 polypeptide also has an amino terminal A domain, a central B domain, and a carboxyl terminal C domain. The three domains of the LEC1 polypeptide are defined as follows: in SEQ ID NO:2, the A domain is located between about amino acid position 1 to about position 27; the B domain is located between about amino acid position 28 to about position 117; and, the C domain is located between about position 118 to about position 208. For the corresponding LEC1 encoding LEC1 nucleotide sequence of SEQ ID NO1: the A domain is located between about nucleotide position 1 to about nucleotide position 81; the B domain is located between about nucleotide position 82 to about nucleotide position 351; the C domain is located between about nucleotide position 352 to about nucleotide position 624.

The DNA binding activity, and, therefore, transcription activation function, of LEC1 polypeptides is thought to be modulated by a short region of seven residues (MPIANVI; SEQ ID NO:5) at residues 34–40 of SEQ ID NO:2. Thus, the polypeptides of the invention will often retain these sequences.

Modified protein chains can also be readily designed utilizing various recombinant DNA techniques well known to those skilled in the art and described for instance, in Sambrook et al., supra. Hydroxylamine can also be used to introduce single base mutations into the coding region of the gene (Sikorski, et al., (1991). Meth. Enzymol. 194: 302–318). For example, the chains can vary from the naturally occurring sequence at the primary structure level by amino acid substitutions, additions, deletions, and the like. These modifications can be used in a number of combinations to produce the final modified protein chain.

Desired modified LEC1 polypeptides can be identified using assays to screen for the presence or absence of wild type LEC1 activity. Such assays can be based on the ability of the LEC1 protein to functionally complement the hap3 mutation in yeast. As noted above, it has been shown that homologs from different species functionally interact with yeast subunits of the CBF. (Sinha, et al., (1995). Proc. Natl. Acad. Sci. USA 92:1624–1628); see, also, Becker, et al., (1991). Proc. Natl. Acad. Sci. USA 88:1968–1972). The reporter for this screen can be any of a number of standard reporter genes such as the lacZ gene encoding beta-galactosidase that is fused with the regulatory DNA sequences and promoter of the yeast CYC1 gene. This promoter is regulated by the yeast CBF.

A plasmid containing the LEC1 cDNA clone is mutagenized in vitro according to techniques well known in the art. The cDNA inserts are excised from the plasmid and inserted into the cloning site of a yeast expression vector such as pYES2 (Invitrogen). The plasmid is introduced into hap3- yeast containing a lacZ reporter that is regulated by the yeast CBF such as pLG265UP1-lacZ (Guarente, et al., (1984) Cell 36: 317–321). Transformants are then selected and a filter assay is used to test colonies for beta-galactosidase activity. After confirming the results of activity assays, immunochemical tests using a LEC1 antibody are performed on yeast lines that lack beta-galactosidase activity to identify those that produce stable LEC1 protein but lack activity. The mutant LEC1 genes are then cloned from the yeast and their nucleotide sequence determined to identify the nature of the lesions.

In other embodiments, the promoters derived from the LEC1 genes of the invention can be used to drive expression of heterologous genes in an embryo-specific or seed-specific manner, such that desired gene products are present in the embryo, seed, or fruit. Suitable structural genes that could be used for this purpose include genes encoding proteins useful in increasing the nutritional value of seed or fruit. Examples include genes encoding enzymes involved in the biosynthesis of antioxidants such as vitamin A, vitamin C, vitamin E and melatonin. Other suitable genes encoding proteins involved in modification of fatty acids, or in the biosynthesis of lipids, proteins, and carbohydrates. Still other genes can be those encoding proteins involved in auxin and auxin analog biosynthesis for increasing fruit size, genes encoding pharmaceutically useful compounds, and genes encoding plant resistance products to combat fungal or other infections of the seed.

Typically, desired promoters are identified by analyzing the 5' sequences of a genomic clone corresponding to the embryo-specific genes described here. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. J. Messing et al., in Genetic Engineering in Plants, pp. 221–227 (Kosage, Meredith and Hollaender, eds. (1983)).

A number of methods are known to those of skill in the art for identifying and characterizing promoter regions in plant genomic DNA (see, e.g., Jordano, et al., Plant Cell, 1: 855–866 (1989); Bustos, et al., Plant Cell, 1:839–854 (1989); Green, et al., EMBO J. 7, 4035–4044 (1988); Meier, et al., Plant Cell, 3, 309–316 (1991); and Zhang, et al., Plant Physiology 110: 1069–1079 (1996)).

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. Ann. Rev. Genet. 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of Agrobacterium tumafaciens, and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers. As noted above, the promoters from the LEC1 genes described here are particularly useful for directing gene expression so that a desired gene product is located in embryos or seeds. Other suitable promoters include those from genes encoding storage proteins or the lipid body membrane protein, oleosin. Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

LEC1 nucleic acid sequences of the invention are expressed recombinantly in plant cells to enhance and increase levels of endogenous LEC1 polypeptides. Alternatively, antisense or other LEC1 constructs (described above) are used to suppress LEC1 levels of expression. A variety of different expression constructs, such as expression cassettes and vectors suitable for transformation of plant cells can be prepared. Techniques for transforming a wide variety of higher plant species are well known and described in the technical and scientific literature. See, e.g., Weising et al. Ann. Rev. Genet. 22:421–477 (1988). A DNA sequence coding for a LEC1 polypeptide, e.g., a cDNA sequence encoding a full length protein, can be combined with cis-acting (promoter) and trans-acting (enhancer) transcriptional regulatory sequences to direct the timing, tissue type and levels of transcription in the intended tissues of the transformed plant. Translational control elements can also be used.

The invention provides a LEC1 nucleic acid operably linked to a promoter which, in a preferred embodiment, is capable of driving the transcription of the LEC1 coding sequence in plants. The promoter can be, e.g., derived from plant or viral sources. The promoter can be, e.g., constitutively active, inducible, or tissue specific. In construction of recombinant expression cassettes, vectors, transgenics, of the invention, a different promoters can be chosen and employed to differentially direct gene expression, e.g., in some or all tissues of a plant or animal.

Typically, desired promoters are identified by analyzing the 5' sequences of a genomic clone corresponding to the embryo-specific genes described here. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions –80 to –100, there is typically a promoter element with a series of adenines surrounding the trinucleotide G (or T) N G. J. Messing et al., in Genetic Engineering in Plants, pp. 221–227 (Kosage, Meredith and Hollaender, eds. (1983)). A number of methods are known to those of skill in the art for identifying and characterizing promoter regions in plant genomic DNA (see, e.g., Jordano, et al., Plant Cell, 1: 855–866 (1989); Bustos, et al., Plant Cell, 1:839–854 (1989); Green, et al., EMBO J. 7, 4035–4044 (1988); Meier, et al., Plant Cell, 3, 309–316 (1991); and Zhang (1996) Plant Physiology 110:1069–1079).

Constitutive Promoters

A promoter fragment can be employed which will direct expression of LEC1 nucleic acid in all transformed cells or tissues, e.g. as those of a regenerated plant. Such promoters are referred to herein as "constitutive" promoters and are active under most environmental conditions and states of development or cell differentiation. Promoters that drive expression continuously under physiological conditions are referred to as "constitutive" promoters and are active under most environmental conditions and states of development or cell differentiation. Examples of constitutive promoters include those from viruses which infect plants, such as the cauliflower mosaic virus (CaMV) 35S transcription initiation region (see, e.g., Dagless (1997) Arch. Virol. 142:183–191); the 1'- or 2'- promoter derived from T-DNA of Agrobacterium tumafaciens (see, e.g., Mengiste (1997) supra; O'Grady (1995) Plant Mol. Biol. 29:99–108); the promoter of the tobacco mosaic virus; the promoter of Figwort mosaic virus (see, e.g., Maiti (1997) Transgenic Res. 6:143–156); actin promoters, such as the Arabidopsis actin gene promoter (see, e.g., Huang (1997) Plant Mol. Biol. 1997 33:125–139); alcohol dehydrogenase (Adh) gene promoters (see, e.g., Millar (1996) Plant Mol. Biol. 31:897–904); and, other transcription initiation regions from various plant genes known to those of skill. See also Holtorf (1995) "Comparison of different constitutive and inducible promoters for the overexpression of transgenes in Arabidopsis thaliana," Plant Mol. Biol. 29:637–646.

Inducible Promoters

Alternatively, a plant promoter may direct expression of the LEC1 nucleic acid of the invention under the influence of changing environmental conditions or developmental conditions. Examples of environmental conditions that may effect transcription by inducible promoters include anaerobic conditions, elevated temperature, drought, or the presence of light. Such promoters are referred to herein as "inducible" promoters. For example, the invention incorporates the drought-inducible promoter of maize (Busk (1997) supra); the cold, drought, and high salt inducible promoter from potato (Kirch (1997) Plant Mol. Biol. 33:897–909).

Alternatively, plant promoters which are inducible upon exposure to plant hormones, such as auxins, are used to express the nucleic acids of the invention. For example, the invention can use the auxin-response elements E1 promoter fragment (AuxREs) in the soybean (Glycine max L.) (Liu (1997) Plant Physiol. 115:397–407); the auxin-responsive Arabidopsis GST6 promoter (also responsive to salicylic acid and hydrogen peroxide) (Chen (1996) Plant J. 10: 955–966); the auxin-inducible parC promoter from tobacco (Sakai (1996) 37:906–913); a plant biotin response element (Streit (1997) Mol. Plant Microbe Interact. 10:933–937); and, the promoter responsive to the stress hormone abscisic acid (Sheen (1996) Science 274:1900–1902).

Plant promoters which are inducible upon exposure to chemicals reagents which can be applied to the plant, such as herbicides or antibiotics, are also used to express the nucleic acids of the invention. For example, the maize In2-2 promoter, activated by benzenesulfonamide herbicide safeners, can be used (De Veylder (1997) Plant Cell Physiol. 38:568–577); application of different herbicide safeners induces distinct gene expression patterns, including expression in the root, hydathodes, and the shoot apical meristem. LEC1 coding sequence can also be under the control of, e.g., a tetracycline-inducible promoter, e.g., as described with transgenic tobacco plants containing the Avena sativa L. (oat) arginine decarboxylase gene (Masgrau (1997) Plant J. 11:465–473); or, a salicylic acid-responsive element (Stange (1997) Plant J. 11:1315–1324.

Tissue-Specific Promoters

Alternatively, the plant promoter may direct expression of the polynucleotide of the invention in a specific tissue (tissue-specific promoters). Tissue specific promoters are transcriptional control elements that are only active in particular cells or tissues at specific times during plant development, such as in vegetative tissues or reproductive tissues. Promoters from the LEC1 genes of the invention are particularly useful for tissue-specific direction of gene expression so that a desired gene product is generated only or preferentially in zygotes, embryos or seeds, as described below.

Examples of tissue-specific promoters under developmental control include promoters that initiate transcription only (or primarily only) in certain tissues, such as vegetative tissues, e.g., roots or leaves, or reproductive tissues, such as fruit, ovules, seeds, pollen, pistils, flowers, or any embryonic tissue. Reproductive tissue-specific promoters may be, e.g., ovule-specific, embryo-specific, endosperm-specific, integument-specific, seed and seed coat-specific, pollen-specific, petal-specific, sepal-specific, or some combination thereof.

Suitable seed-specific promoters are derived from the following genes: MAC1 from maize, Sheridan (1996) Genetics 142:1009–1020; Cat3 from maize, GenBank No. L05934, Abler (1993) Plant Mol. Biol. 22:10131–1038; vivparous-1 from Arabidopsis, Genbank No. U93215; atmyc1 from Arabidopsis, Urao (1996) Plant Mol. Biol. 32:571–57; Conceicao (1994) Plant 5:493–505; napA from Brassica napus, GenBank No. J02798, Josefsson (1987) JBL 26:12196–1301; the napin gene family from Brassica napus, Sjodahl (1995) Planta 197:264–271.

The ovule-specific BEL1 gene described in Reiser (1995) Cell 83:735–742, GenBank No. U39944, can also be used. See also Ray (1994) Proc. Natl. Acad. Sci. USA 91:5761–5765. The egg and central cell specific FIE1 promoter is also a useful reproductive tissue-specific promoter.

Sepal and petal specific promoters are also used to express LEC1 nucleic acids in a reproductive tissue-specific manner. For example, the Arabidopsis floral homeotic gene APETALA1 (AP1) encodes a putative transcription factor that is expressed in young flower primordia, and later becomes localized to sepals and petals (see, e.g., Gustafson-Brown (1994) Cell 76:131–143; Mandel (1992) Nature 360:273–277). A related promoter, for AP2, a floral homeotic gene that is necessary for the normal development of sepals and petals in floral whorls, is also useful (see, e.g., Drews (1991) Cell 65:991–1002; Bowman (1991) Plant Cell 3:749–758). Another useful promoter is that controlling the expression of the unusual floral organs (ufo) gene of Arabidopsis, whose expression is restricted to the junction between sepal and petal primordia (Bossinger (1996) Development 122:1093–1102).

A maize pollen-specific promoter has been identified in maize (Guerrero (1990) Mol. Gen. Genet. 224:161–168). Other genes specifically expressed in pollen are described, e.g., by Wakeley (1998) Plant Mol. Biol. 37:187–192; Ficker (1998) Mol. Gen. Genet. 257:132–142; Kulikauskas (1997) Plant Mol. Biol. 34:809–814; Treacy (1997) Plant Mol. Biol. 34:603–611.

Other suitable promoters include those from genes encoding embryonic storage proteins. For example, the gene encoding the 2S storage protein from Brassica napus, Dasgupta (1993) Gene 133:301–302; the 2s seed storage protein gene family from Arabidopsis; the gene encoding oleosin 20 kD from Brassica napus, GenBank No. M63985; the genes encoding oleosin A, Genbank No. U09118, and, oleosin B, Genbank No. U09119, from soybean; the gene encoding oleosin from Arabidopsis, Genbank No. Z17657; the gene encoding oleosin 18 kD from maize, GenBank No. J05212, Lee (1994) Plant Mol. Biol. 26:1981–1987; and, the gene encoding low molecular weight sulphur rich protein from soybean, Choi (1995) Mol Gen, Genet. 246:266–268, can be used. The tissue specific E8 promoter from tomato is particularly useful for directing gene expression so that a desired gene product is located in fruits.

A tomato promoter active during fruit ripening, senescence and abscission of leaves and, to a lesser extent, of flowers can be used (Blume (1997) Plant J. 12:731–746). Other exemplary promoters include the pistol specific promoter in the potato (Solanum tuberosum L.) SK2 gene, encoding a pistil-specific basic endochitinase (Ficker (1997) Plant Mol. Biol. 35:425–431); the Blec4 gene from pea (Pisum sativum cv. Alaska), active in epidermal tissue of vegetative and floral shoot apices of transgenic alfalfa. This makes it a useful tool to target the expression of foreign genes to the epidermal layer of actively growing shoots.

A variety of promoters specifically active in vegetative tissues, such as leaves, stems, roots and tubers, can also be used to express the LEC1 nucleic acids of the invention. For example, promoters controlling patatin, the major storage protein of the potato tuber, can be used, see, e.g., Kim (1994) Plant Mol. Biol. 26:603–615; Martin (1997) Plant J. 11:53–62. The ORF13 promoter from Agrobacterium rhizogenes which exhibits high activity in roots can also be used (Hansen (1997) Mol. Gen. Genet. 254:337–343. Other useful vegetative tissue-specific promoters include: the tarin promoter of the gene encoding a globulin from a major taro (Colocasia esculenta L. Schott) corm protein family, tarin (Bezerra (1995) Plant Mol. Biol. 28:137–144); the curculin promoter active during taro corm development (de Castro (1992) Plant Cell 4:1549–1559) and the promoter for the tobacco root-specific gene TobRB7, whose expression is localized to root meristem and immature central cylinder regions (Yamamoto (1991) Plant Cell 3:371–382).

Leaf-specific promoters, such as the ribulose biphosphate carboxylase (RBCS) promoters can be used. For example, the tomato RBCS 1, RBCS2 and RBCS3A genes are expressed in leaves and light-grown seedlings, only RBCS1 and RBCS2 are expressed in developing tomato fruits (Meier (1997) FEBS Lett. 415:91–95). A ribulose bisphosphate carboxylase promoters expressed almost exclusively in mesophyll cells in leaf blades and leaf sheaths at high levels, described by Matsuoka (1994) Plant J. 6:311–319, can be used. Another leaf-specific promoter is the light harvesting chlorophyll a/b binding protein gene promoter, see, e.g., Shiina (1997) Plant Physiol. 115:477–483; Casal (1998) Plant Physiol. 116:1533–1538. The Arabidopsis thaliana myb-related gene promoter (Atmyb5) described by Li (1996) FEBS Lett. 379:117–121, is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16 cell stage of embryo development and persists beyond the heart stage. A leaf promoter identified in maize by Busk (1997) Plant J. 11: 1285–1295, can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio (1996) Cell 86:423–433; and, Long (1996) Nature 379:66–69; can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto (1995) Plant Cell. 7:517–527). Also useful are kn1-related genes from maize and other species which show meristem-specific expression, see, e.g., Granger (1996) Plant Mol. Biol. 31:373–378; Kerstetter (1994) Plant Cell 6:1877–1887; Hake (1995) Philos. Trans. R. Soc. Lond. B. Biol. Sci. 350:45–51. For example, the Arabidopsis thaliana KNAT1 promoter. In the shoot apex, KNAT1 transcript is localized primarily to the shoot apical meristem; the expression of KNAT1 in the shoot meristem decreases during the floral transition and is restricted to the cortex of the inflorescence stem (see, e.g., Lincoln (1994) Plant Cell 6:1859–1876).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, a LEC1 nucleic acid is expressed through a transposable element. This allows for constitutive, yet periodic and infrequent expression of the constitutively active polypeptide. The invention also provides for use of tissue-specific promoters derived from viruses which can include, e.g., the tobamovirus subgenomic promoter (Kumagai (1995) Proc. Natl. Acad. Sci. USA 92:1679–1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) Plant Mol. Biol. 31:1129–1139).

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional Agrobacterium tumefaciens host vector. The virulence functions of the Agrobacterium tumefaciens host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. Embo J. 3:2717–2722 (1984). Electroporation techniques are described in Fromm et al. Proc. Natl. Acad. Sci. USA 82:5824 (1985). Ballistic transformation techniques are described in Klein et al. Nature 327:70–73 (1987).

Agrobacterium tumefaciens-mediated transformation techniques, including disarming and use of binary vectors, are well described in the scientific literature. See, for example Horsch et al. Science 233:496–498 (1984), and Fraley et al. Proc. Natl. Acad. Sci. USA 80:4803 (1983).

Transformed plant cells which are derived by any of the above transformation techniques can be cultured to regenerate a whole plant which possesses the transformed genotype and thus the desired phenotype such as seedlessness. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124–176, MacMillilan Publishing Company, New York, 1983; and Binding, Regeneration of Plants, Plant Protoplasts, pp. 21–73, CRC Press, Boca Raton, 1985. Regeneration can also be obtained from plant callus, explants, organs, or parts thereof Such regeneration techniques are described generally in Klee et al. Ann. Rev. of Plant Phys. 38:467–486 (1987).

The nucleic acids of the invention can be used to confer desired traits on essentially any plant. Thus, the invention has use over a broad range of plants, including species from the genera Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna, and, Zea. The LEC1 genes of the invention are particularly useful in the production of transgenic plants in the genus Brassica. Examples include broccoli, cauliflower, brussel sprouts, canola, and the like.

Use and Recombinant Expression of LEC1 in Combination with other Genes

The LEC1 nucleic acids of the invention can be expressed together with other structural or regulatory genes to achieve a desired effect. A cell or plant, such as a transformed cell or a transgenic plant, can be transformed, engineered or bred to co-express both LEC1 nucleotide and/or LEC1 polypeptide, and another gene or gene product.

The LEC1 nucleic acids of the invention, when expressed in plant reproductive or vegetative tissue, can induce ectopic embryo morphogenesis. Thus, in one embodiment, a LEC1 nucleic acid of the invention is expressed in a sense conformation in a transgenic plant to induce the expression of ectopic embryo-like structures, as discussed above. In another embodiment, LEC1 is co-expressed with a gene or nucleic acid that increases reproductive tissue mass, e.g., increases fruit size, seed mass, seed protein or seed oils. For example, co-expression of antisense nucleic acid to ADC genes, such as AP2 and RAP2 genes of Arabidopsis, will dramatically increase seed mass, seed protein and seed oils; see, e.g., Jofiuku, et al., WO 98/07842; Okamuro (1997) Proc. Natl. Acad. Sci. USA 94:7076–7081; Okamuro (1997) Plant Cell 9:37–47; Jofuku (1994) Plant Cell 6:1211–1225. Thus, co-expression of a LEC1 of the invention, to induce ectopic expression of embronic cells and tissues, together with another plant nucleic acid and/or protein, such as the seed-mass enhancing antisense AP2 nucleic acid, generates a cell, tissue, or plant (e.g., a transgenic plant) with increased fruit and seed mass, greater yields of embryonic storage proteins, and the like.

In another embodiment, the LEC1 nucleic acids of the invention are expressed in plant reproductive or vegetative cells and tissues which lack the ability to produce functional ADC genes, such as AP2 and RAP2 genes. The LEC1 nucleic acid can be expressed in an ADC "knockout" transgenic plant. Alternatively, the LEC1 nucleic acid can be expressed in a cell, tissue or plant expressing a mutant ADC nucleic acid or gene product. Expression of LEC1 nucleic acid in any of these non-functioning ADC models will also produce a cell, tissue or plant with increased fruit and seed mass, greater yields of embryonic storage proteins, and the like.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

EXAMPLE 1

This example describes the isolation and characterization of an exemplary LEC1 gene.

Experimental Procedures

Plant Material

A lec1-2 mutant was identified from a population of Arabidopsis thaliana ecotype Wassilewskija (Ws-O) lines mutagenized with T-DNA insertions as described before (West et al., 1994). The abi3-3, fus3-3 and lec1-1 mutants were generously provided by Peter McCourt, University of Toronto and David Meinke, Oklahoma State University. Wild type plants and mutants were grown under constant light at 22° C.

Double mutants were constructed by intercrossing the mutant lines lec1-1, lec1-2, abi3-3, fus3-3, and lec2. The genotype of the double mutants was verified through backcrosses with each parental line. Double mutants were those who failed to complement both parent lines. Homozygous single and double mutants were generated by germinating intact seeds or dissected mature embryos before desiccation on basal media.

Isolation and Sequence Analysis of Genomic and cDNA Clones

Genomic libraries of Ws-O wild type plants, lec1-1 and lec1-2 mutants were made in GEM11 vector according to the instructions of the manufacturer (Promega). Two silique-specific cDNA libraries (stages globular to heart and heart to young torpedo) were made in ZAPII vector (Stratagene).

The genomic library of lec1-2 was screened using right and left T-DNA specific probes according to standard techniques. About 12 clones that cosegregate with the mutation, were isolated and purified and the entire DNAs were further labeled and used as probes to screen a southern blot containing wild type and lec1-1 genomic DNA. One clone hybridized with plant DNA and was further analyzed. A 7.1 kb XhoI fragment containing the left border and the plant sequence flanking the T-DNA was subcloned into pBluescript-KS plasmid (Stratagene) to form ML7 and sequenced using a left border specific primer (5' GCATA-GATGCACTCGAAATCAGCC 3'; (SEQ ID NO:13). The T-DNA organization was partially verified using southern analysis with T-DNA left and right borders and PBR322 probes. The results suggested that the other end of the T-DNA is also composed of left border. This was confirmed by generating a PCR fragment using a genomic plant DNA primer (LP primer 5' GCT CTA GAC ATA CAA CAC TTT TCC TTA 3'; SEQ ID NO:8) and a T-DNA left border specific primer (5' GCTTGGTAATAATTGTCATTAG 3'; SEQ ID NO:14) and sequencing.

The EcoRI insert of ML7 was used to screen a wild type genomic library. Two overlapping clones were purified and a 7.4 EcoRI genomic fragment from the wild type DNA region was subcloned into pBluescript-KS plasmid making WT74. This fragment was sequenced (SEQ ID NO:4) and was used to screen lec1-1 genomic library and wild type silique-specific cDNA libraries. 8 clones from the lec1-1 genomic library were identified and analyzed by restriction mapping.

From these clones the exact site of the deletion in lec1-1 was mapped and sequenced by amplifying a Xbp PCR fragment using primers (H21-5' CTA AAA ACA TCT ACG GTT CA 3' (SEQ ID NO:15); H 17-5' TTT GTG GTT GAC CGT TTG GC 3' (SEQ ID NO:16) flanking the deletion region in lec1-1 genomic DNA. Clones were isolated from both cDNA libraries and partially sequenced. The sequence of the cDNA clones and the wild type genomic clone matched exactly, confirming that both derived from the same locus. All hybridizations were performed under stringent conditions with 32P random prime probes (Stratagene).

Sequencing was done using the automated dideoxy chain termination method (Applied Biosystems, Foster City, Calif.). Data base searches were performed at the National Center for Biotechnology Information by using the BLAST network service. Alignment of protein sequences was done using PILEUP program (Genetics Computer Group, Madison, Wis.)

DNA and RNA Blot Analysis

Genomic DNA was isolated from leaves by using the CTAB-containing buffer Dellaporta, et al., (1983). Plant Mol. Biol. Reporter 1: 19–21. Two micrograms of DNA was digested with different restriction endonucleases, electrophoretically separated in 1% agarose gel, and transferred to a nylon membrane (Hybond N; Amersham).

Total RNA was prepared from siliques, two days old seedlings, stems, leaves, buds and roots. Poly(A)+RNA was purified from total RNA by oligo(dT) cellulose chromatography, and two micrograms of each Poly(A)+ RNA samples were separated in 1% denatured formaldehyde-agarose gel. Hybridizations were done under stringent conditions unless it specifies otherwise. Radioactive probes were prepared as described above.

Complementation of lec1 Mutants

A 3.4 kb BstyI fragment of genomic DNA (SEQ ID NO:3) containing sequences from 1.992 kb upstream of the ORF to a region 579 bp downstream from the poly A site was subcloned into the hygromycin resistant binary vector pBIB-Hyg. The LEC1 cDNA was placed under the control of the 35S promoter and the ocs polyadenylation signals by inserting a PCR fragment spanning the entire coding region into the plasmid pART7. The entire regulatory fragment was then removed by digestion with NotI and transferred into the hygromycin resistant binary vector BJ49. The binary vectors were introduced into the Agrobacterium strain GV3101, and constructions were checked by re-isolation of the plasmids and restriction enzyme mapping, or by PCR. Transformation to homozygous lec1-1 and lec1-2 mutants were done using the in planta transformation procedure (Bechtold, et al., (1993). Comptes Rendus de l'Academie des Sciences Serie III Sciences de la Vie, 316: 1194–1199. Dry seeds from lec1 mutants were selected for transformants by their ability to germinate after desiccation on plates containing 5 g/ml hygromycin. The transformed plants were tested for the present of the transgene by PCR and by screening the siliques for the present of viable seeds.

In Situ Hybridization

Experiments were performed as described previously by Dietrich et al. (1989) Plant Cell 1: 73–80. Sections were hybridized with LEC1 antisense probe. As a negative control, the LEC1 antisense probe was hybridized to seed sections of lec1 mutants. In addition, a sense probe was prepared and reacted with the wild type seed sections.

Results

Genetic Interaction Between Leafy Cotyledon-Type Mutants and abi3

In order to understand the genetic pathways which regulate late embryogenesis we took advantage of three Arabidopsis mutants lec2, fus3-3 and abi3-3 that cause similar defects in late embryogenesis to those of lec1-1 or lec1-2. These mutants are desiccation intolerant, sometimes viviparous and have activated shoot apical meristems. The lec2 and fus3-3 mutants are sensitive to ABA and possess trichomes on their cotyledons and therefore can be categorized as leafy cotyledon-type mutants (Meinke et al., 1994). The abi3-3 mutants belong to a different class of late embryo defective mutations that is insensitive to ABA and does not have trichomes on the cotyledons.

The two classes of mutants were crossed to lec1-1 and lec1-2 mutants to construct plants homozygous to both mutations. The lec1 and lec2 mutations interact synergistically, resulting in a double mutant which is arrested in a stage similar to the late heart stage, the double mutant embryo, however, is larger. The led or lec2 and fus3-3 double mutants did not display any epistasis and the resulting embryo had an intermediate phenotype. The lec1/abi3-3 double mutants and lec2/abi3-3 double mutants were ABA insensitive and had a lec-like phenotype. There was no different between double mutants that consist of either lec1-1 or lec1-2.

No epistasis was seen between the double mutants indicating that each of the above genes, the LEC-type and ABI3 genes, operate in different genetic pathways.

LEC1 Functions Early in Embryogenesis

The effects of lec1 is not limited to late embryogenesis, it also has a role in early embryogenesis. The embryos of the lec1/lec2 double mutants were arrested in the early stages of development, while the single mutants developed into mature embryos, suggesting that these genes act early during development.

Further examination of the early stages of the single and double mutations showed defects in the shape, size and cell division pattern of the mutants suspensors. The suspensor of wild type embryo consists of a single file of six to eight cells, whereas the suspensors of the mutants are often enlarged and undergo periclinal divisions. Leafy cotyledon mutants exhibit suspensor anomalies at the globular or transition stage whereas wild type and abi3 mutant do not show any abnormalities.

The number of anomalous suspensors increases as the embryos continue to develop. At the torpedo stage, the wild type suspensor cells undergo programmed cell death, but in the mutants secondary embryos often develop from the abnormal suspensors and, when rescued, give rise to twins.

The Organization of the LEC1 Locus in Wild Type Plants and lec1 Mutants

Two mutant alleles of the LEC1 gene have been reported, lec1-1 and lec1-2 (Meinke, 1992; West et al., 1994). Both mutants were derived from a population of plants mutagenized insertionally with T-DNA (Feldmann and Marks, 1987), although lec1-1 is not tagged. The lec1-2 mutant contains multiple T-DNA insertions. A specific subset of T-DNA fragments were found to be closely linked with the mutation. A genomic library of lec1-2 was screened using right and left borders T-DNA as probes. Genomic clones containing T-DNA fragments that cosegregate with the mutation were isolated and tested on Southern blots of both wild type and lec1-1 plants. Only one clone hybridized with Arabidopsis DNA and also gave polymorphic restriction fragment in lec1-1.

The lec1-1 polymorphism resulted from a small deletion, approximately 2 kb in length. Using sequences from the plant fragment flanking the T-DNA, the genomic wild type DNA clones and the lec1-1 genomic clones were isolated. An EcoRI fragment of 7.4 kb of the genomic wild type DNA that corresponded to the polymorphic restriction fragment in lec1-1 was further analyzed and sequenced. The exact site of the deletion in lec1-1 was identified using a PCR fragment that was generated by primers, within the expected borders of the deleted fragment, and sequencing.

In the wild type genomic DNA that corresponded to the lec1-1 deletion, a 626 bp ORF was identified. Southern analysis of wild type DNA and the two mutants DNA probed with the short DNA fragment of the ORF revealed that both the wild type and lec1-2 DNA contain the ORF while the lec1-1 genomic DNA did not hybridize. The exact insertion site of the T-DNA in lec1-2 mutant was determined by PCR and sequencing and it was found that the T-DNA was inserted 115 bp upstream of the ORF's translational initiation codon in the 5'

In order to isolate the LEC1 gene two cDNA libraries of young siliques were screened using the 7.4 kb DNA fragment as a probe. Seventeen clones were isolated and after further analysis and partial sequencing they were all found to be identical to the genomic ORF. The cDNA contains 626 bp ORF specifying 208 amino acid protein (SEQ ID NO:1 and SEQ ID NO:2).

The LEC1 cDNA was used to hybridize a DNA gel blot containing Ws-O genomic DNA digested with three different restriction enzymes. Using low stringency hybridization we found that there is at least one more gene. This confirmed our finding of two more Arabidopsis ESTs that show homology to the LEC1 gene.

The LEC1 Gene is Embryo Specific

The lec1 mutants are affected mostly during embryogenesis. Rescued mutants can give rise to homozygous plants that have no obvious abnormalities other than the presence of trichomes on their cotyledons and their production of defective progeny. Therefore, we expected the LEC1 gene to have a role mainly during embryogenesis and not during vegetative growth. To test this assumption poly (A)+RNA was isolated from siliques, seedling, roots, leaves, stems and buds of wild type plants and from siliques of lec1 plants. Only one band was detected on northern blots using either the LEC1 gene as a probe or the 7.4 kb genomic DNA fragment suggesting that there is only one gene in the genomic DNA fragment which is active transcriptionally. The transcript was detected only in siliques containing young and mature embryos and was not detected in seedlings, roots, leaves, stems and buds indicating that the LEC1 gene is indeed embryo specific. In addition, no RNA was detected in siliques of both alleles of lec1mutants confirming that this ORF corresponds to the LEC1 gene.

Expression Pattern of the LEC1 Gene

To study how the LEC1 gene specifies cotyledons identity, we analyzed its expression by in situ hybridization. We specifically focused on young developing embryos since the mutants abnormal suspensors phenotype indicates that the LEC1 gene should be active very early during development.

During embryogenesis, the LEC1 transcript was first detected in proglobular embryos. The transcript was found in all cells of the proembryo and was also found in the suspensor and the endosperm. However, from the globular stage and on it accumulates more in the outer layer of the embryo, namely the protoderm and in the outer part of the ground meristem leaving the procambium without a signal. At the torpedo stage the signal was stronger in the cotyledons and the root meristem, and was more limited to the protoderm layer. At the bent cotyledon stage the signal was present throughout the embryo and at the last stage of development when the embryo is mature and filling the whole seed we could not detect the LEC1 transcript. This might be due to sensitivity limitation and may imply that if the LEC1 transcript is expressed at that stage it is not localized in the mature embryo, but rather spread throughout the embryo.

The LEC1 Gene Encodes a Homolog of CCAAT Binding Factor

Comparison of the deduced amino acid sequence of LEC1 to the GenBank reveals significant similarity to a subunit of a transcription factor, the CCAAT box binding factor (CBF). CBFs are highly conserved family of transcription factors that regulate gene activity in eukaryotic organisms Mantvani, et al., . (1992). Nucl. Acids Res. 20: 1087–1091.

They are hetero-oligomeric proteins that consist of between three to four non-homologous subunits. LEC1 was found to have high similarity to CBF-A subunit. This subunit has three domains; A and C which show no conservation between kingdoms and a central domain, B, which is highly conserved evolutionary. Similarly the LEC1 gene is composed of three domains. The LEC1 B domain shares between 75%–85% similarity and 55%–63% identity with different B domains that are found in organisms ranging from yeast to human. Within this central domain, two highly conserved amino acid segments are present. Deletion and mutagenesis analysis in the CBF-A yeast homolog hap3 protein demonstrated that a short region of seven residues (42–48) (LPIANVA; SEQ ID NO:17) is required for binding the CCAAT box, while the subunit interaction domain lies in the region between residues 69–80 (MQECVSEFISFV; SEQ ID NO:18) (Xing et al., supra). LEC1 protein shares high homology to those regions.

DISCUSSION

The lec1 mutant belongs to the leafy cotyledon class that interferes mainly with the embryo program and therefore is thought to play a central regulatory role during embryo development. It was shown before that LEC1 gene activity is required to suppress germination during the maturation stage. Therefore, we analyzed the genetic interaction of homozygous double mutants of the different members of the leafy cotyledon class and the abi3 mutant that has an important role during embryo maturation. All the five different combinations of the double mutants showed either an intermediate phenotype or an additive effect. No epistatic relationship among the four genes was found. These findings suggest that the different genes act in parallel genetic pathways. Of special interest was the double mutant lec1/lec2 that was arrested morphologically at the heart stage, but continued to grow in that shape. This double mutant phenotype indicates that both genes LEC1 and LEC2 are essential for early morphogenesis and their products may interact directly or indirectly in the young developing embryo.

The Role of LEC1 in Embryogenesis

One of the proteins that mediate CCAAT box function, is an heteromeric protein called CBF (also called NFY or CP1). CBF is a transcription activator that regulates constitutively expressed genes, but also participates in differential activation of developmental genes Wingender, E. (1993). Gene Regulation in Eukaryotes (New York: VCH Publishers). In mammalian cells, three subunits have been identified CBF-A, CBF-B and CBF-C and all of which are required for DNA binding. In yeast, the CBF homolog HAP activates the CYC1 and other genes involved in the mitochondrial electron transport Johnson, et al., Proteins. Annu. Rev. Biochem. 58, 799–840. (1989). HAP consists of four subunits hap2, hap3, hap4 and hap5. Only hap2, 3 and 5 are required for DNA binding. CBF-A, B and C show high similarity to the yeast hap3, 2 and 5, respectively. It was also reported that mammalian CBF-A and B can be functionally interchangeable with the corresponding yeast subunits (Sinha et al., supra.).

The LEC1 gene encodes a protein that shows more then 75% similarity to the conserved region of CBF-A. CCAAT motifs are not common in plants' promoters and their role in transcription regulation is not clear. However, maize and Brassica homologs have been identified Search in the Arabidopsis GenBank revealed several ESTs that show high similarity to CBF-A, B and C. Accession numbers of CBF-A (HAP3) homologs: H37368, H76589; CBF-B (HAP2) homologs: T20769; CBF-C (HAP5) homologs: T43909, T44300. These findings and the pleiotropic affects of LEC1 suggest that LEC1 is a member of a heteromeric complex that functions as a transcription factor.

The model suggests that LEC1 acts as transcription activator to several sets of genes, which keep the embryonic program on and repress the germination process. Defective LEC1 expression partially shuts down the embryonic program and as a result the cotyledons lose their embryonic characteristics and the germination program is active in the embryo.

EXAMPLE 2

This example demonstrates that LEC1 is sufficient to induce embryonic pathways in transgenic plants.

The phenotype of lec1 mutants and the gene's expression pattern indicated that LEC1 functions specifically during embryogenesis. A LEC1 cDNA clone under the control of the cauliflower mosaic virus 35S promoter was transferred into lec1-1 mutant plants in planta using standard methods as described above.

Viable dry seeds were obtained from lec1-1 mutants transformed with the 35/LEC1 construct. However, the transformation efficiency was only approximately 0.6% of that obtained normally. In several experiments, half the seeds that germinated (12/23) produced seedlings with an abnormal morphology. Unlike wild type seedlings, these 35S/LEC1 seedlings possessed cotyledons that remained fleshy and that failed to expand. Roots often did not extend or extended abnormally and sometimes greened. These seedlings occasionally produced a single pair of organs on the shoot apex at the position normally occupied by leaves. Unlike wild type leaves, these organs did not expand and did not possess trichomes. Morphologically, these leaf-like structures more closely resembled embryonic cotyledons than leaves.

The other 35S/LEC1 seeds that remained viable after drying produced plants that grow vegetatively. The majority of these plants (7) flowered and produced 100% lec1mutant seeds. Amplification experiments confirmed that the seedlings contained the transgene, suggesting that the 35S/LEC1 gene was inactive in these T2 seeds. No vegetative abnormalities were observed in these plants with the exception that a few displayed defects in apical dominance. A few plants (2) were male sterile and did not produce progeny. One plant that produced progeny segregated 25% mutant Lec1⁻ seeds that, when germinated before desiccation and grown to maturity, gave rise to 100% mutant seed, as expected for a single transgene locus. The other 75% of seeds contained embryos with either a wild type phenotype or a phenotype intermediate between lec1 mutants and wild type. Only 25% of the dry seed from this plant germinated, and all seedlings resembled the embryo-like seedlings described above. Some seedlings continued to grow and displayed a striking phenotype. These 35S/LEC1 plants developed two types of structures on leaves. One type resembled embryonic cotyledons while the other looked like intact torpedo stage embryos. Thus, ectopic expression of LEC1 induces the morphogenesis phase of embryo development in vegetative cells.

Because many 35S/LEC1 seedlings exhibited embryonic characteristics, the seedlings were analyzed for expression of genes specifically active in embryos. Cruciferin A storage protein mRNA accumulated throughout the 35S/LEC1 seedlings, including the leaf-like structures. Proteins with sizes characteristic of 12S storage protein cruciferin accumulated in these transgenic seedlings. Thus, 35S/LEC1 seedings displaying an embryo-like phenotype accumulated embryo-specific mRNAs and proteins. LEC1 mRNA accumulated to a high level in these 35S/LEC1 seedlings in a pattern similar to early stage embryos but not in wild type seedlings. LEC1 is therefore sufficient to alter the fate of vegetative cells by inducing embryonic programs of development.

The ability of LEC1 to induce embryonic programs of development in vegetative cells establishes the gene as a central regulator of embryogenesis. LEC1 is sufficient to induce both the seed maturation pathway as indicated by the induction of storage protein genes in the 35S/LEC1 seedlings. The presence of ectopic embryos on leaf surfaces and cotyledons at the position of leaves also shows that LEC1 can activate the embryo morphogenesis pathway. Thus, LEC1 regulates both early and late embryonic processes.

EXAMPLE 3

This example shows that LEC1 is expressed in zygotes and that the promoters of the invention can therefore be used to target expression in zygotes.

To determine precisely when the LEC1 gene becomes activated, LEC1 RNA levels were analyzed in the egg apparatus of mature female garnetophytes before fertilization, in zygotes after fertilization, and in very early stage embryos containing an apical cell and two to three suspensor cells. In situ hybridization experiments showed that LEC1 RNA was present in zygotes and early stage embryos but was not detected in female gametophytes. These results show that the LEC1 promoter becomes active in the zygote. The LEC1 is therefore useful to target the expression of sense or antisense versions of regulatory genes or cytotoxic genes to zygotes and early stage embryos.

The above examples are provided to illustrate the invention but not to limit its scope. Other variants of the invention will be readily apparent to one of ordinary skill in the art and are encompassed by the appended claims. All publications, databases, Genbank sequences, patents, and patent applications cited herein are hereby incorporated by reference.

What is claimed is:

1. A method of targeting expression of a polynucleotide in a seed, the method comprising introducing into a plant a LEC1 promoter operably linked to a heterologous polynucleotide sequence, wherein the LEC1 promoter is at least 70% identical to a polynucleotide sequence consisting of nucleotides 1 to 1998 of SEQ ID NO:3.

2. The method of claim 1, wherein the heterologous polynucleotide sequence encodes a desired polypeptide.

3. The method of claim 1, wherein the heterologous polynucleotide sequence is linked to the promoter in an antisense orientation.

4. The method of claim 1, wherein expression of the heterologous polynucleotide sequence is targeted to the embryo.

5. The method of claim 1, wherein the LEC1 promoter is SEQ ID NO:3.

6. A method of targeting expression of a polynucleotide in a zygote, the method comprising introducing into a plant a LEC1 promoter operably linked to a heterologous polynucleotide sequence, wherein the LEC1 promoter is at least 70% identical to a polynucleotide sequence consisting of nucleotides 1 to 1998 of SEQ ID NO:3.

7. The method of claim 6, wherein the LEC1 promoter is SEQ ID NO:3.

8. The method of claim 1, wherein the LEC1 promoter comprises about the first 4.4 kilobases of SEQ ID NO:4.

9. The method of claim 6, wherein the LEC1 promoter comprises about the first 4.4 kilobases of SEQ ID NO;4.

* * * * *